United States Patent
Mewshaw et al.

(10) Patent No.: US 6,291,683 B1
(45) Date of Patent: Sep. 18, 2001

(54) N-ARLOXYETHYL-ALKYLAMINES FOR THE TREATMENT OF DEPRESSION

(75) Inventors: Richard E. Mewshaw, Princeton; Dahui Zhou, Highland Park, both of NJ (US)

(73) Assignee: American Home Products Corp, Madison, NJ (US)

( * ) Notice: Subject to any disclaimer, the term of this patent is extended or adjusted under 35 U.S.C. 154(b) by 0 days.

(21) Appl. No.: 09/593,267

(22) Filed: Jun. 13, 2000

Related U.S. Application Data

(62) Division of application No. 09/287,831, filed on Apr. 7, 1999.
(60) Provisional application No. 60/092,116, filed on Apr. 8, 1998, now abandoned.

(51) Int. Cl.[7] ..................... A61K 31/405; A61K 31/404; C07D 209/04
(52) U.S. Cl. ..................... 548/452; 514/414; 514/419; 548/467; 548/452; 548/486; 548/492; 548/507
(58) Field of Search ..................... 548/467, 486, 548/492, 507, 452; 514/415, 414, 419

(56) References Cited

U.S. PATENT DOCUMENTS

| | | |
|---|---|---|
| 3,371,098 | 2/1968 | Kralt et al. |
| 4,314,943 | 2/1982 | Kreighbaum et al. |
| 5,436,264 * | 7/1995 | Pfister et al. |
| 5,750,724 | 5/1998 | Kang et al. |

FOREIGN PATENT DOCUMENTS

| | | |
|---|---|---|
| 0025727 | 3/1981 | (EP) . |
| 0478954 | 4/1992 | (EP) . |
| 0722941 | 7/1996 | (EP) . |
| 5255302 | 10/1993 | (JP) . |
| 9040648 | 2/1997 | (JP) . |
| 9626923 | 9/1996 | (WO) . |

OTHER PUBLICATIONS

Le Poul et al., *Arch. Pharmacol.*, 352:141 (1995).
Artigas et al., *Trends Neurosci.*, 19:378–383 (1996).
Sleight, A.J. et al., "Identification of 5-hydroxytryptamine1 A Receptor Agents Using a Composite Pharmacophore Analysis and Chemical Database Screening", *Naunyn-Schmiedeberg's Archives of Pharmacology*, 343: 109–16 (1991).

Glennon, R.A., "Concepts for the design of 5-HT1A serotonin agonists and antagonists", *Drug Development Research*, 26(3): 251–274 (1992).

Nelson, D.L., "Structure–Activity Relationships at 5-HT1A receptors: Binding Profiles and Intrinsic Activity", *Pharmacology Biochemistry & Behavior*, 40(4): 1041–51 (1991).

* cited by examiner

Primary Examiner—Alan L. Rotman
Assistant Examiner—Rita Desai
(74) Attorney, Agent, or Firm—Joseph M. Mazzarese

(57) ABSTRACT

Compounds useful for alleviating symptoms of depression are provided which have the following formula:

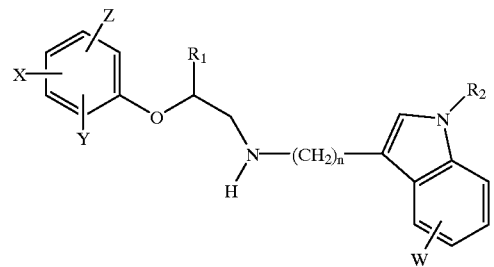

wherein:

$R_1$ is hydrogen, lower alkyl or aryl;

$R_2$ is hydrogen, lower alkyl, phenyl or substituted phenyl;

X and Y are each, independently, hydrogen, lower alkyl, lower alkoxy, or halogen, or together combine with the carbon atoms to which they are attached to complete a cyclopentyl, cyclohexyl, phenyl, pyrrolyl, pyranyl, pyridinyl, dihydrofuranyl, furanyl, dioxanyl, oxazolyl or isoxazolyl group;

Z is hydrogen, halogen or lower alkoxy; with the proviso that when X, Y or Z represent lower alkoxy, they are not present at the ortho position;

W is hydrogen, halogen, lower alkyl, cyano or a trifluoromethyl group; and n is 2–5; or pharmaceutically acceptable salts thereof.

10 Claims, No Drawings

N-ARLOXYETHYL-ALKYLAMINES FOR THE TREATMENT OF DEPRESSION

CROSS REFERENCE TO RELATED APPLICATIONS

The present application is a divisional of U.S. patent application Ser. No. 09/287,831 filed Apr. 7, 1999, allowed Apr. 24, 2000, which claims the benefit of U.S. Provisional Application No. 60/092,116, which was converted from U.S. patent application Ser. No. 09/057,252, filed Apr. 8, 1998 now abandoned, pursuant to a petition filed under 37 C.F.R. 1.53(c)(2)(i) filed May 6, 1998.

FIELD OF INVENTION

The present invention relates to compounds useful for the treatment of diseases affected by disorders of the serotonin-affected neurological systems. More specifically, the present invention is directed to aryloxyethyl-indoly-alkylamine derivatives useful for the treatment of such diseases.

BACKGROUND OF INVENTION

Pharmaceuticals which enhance neurotransmission of serotonin (5-HT) are useful for the treatment of many psychiatric disorders, including depression and anxiety. The first generation of non-selective serotonin-affecting compounds operated through a variety of physiological means which caused them to possess numerous undesired side effects, such as dry mouth, blurred vision, and sedation due to multiple receptor activities. The more recently introduced compounds, i.e., the selective serotonin reuptake inhibitors (SSRIs), act predominately by inhibiting 5-HT, which is released at the synapses, from being actively removed from the synaptic cleft via a presynaptic serotonin transport carrier. As SSRIs require several weeks before they exert their fill therapeutic effect, this 5-HT blockade mechanism cannot fully account for their therapeutic activity. It is speculated that this two week induction which occurs before a fill antidepressant effect is observed, is due to the involvement of the 5-HT1A autoreceptors which suppress the firing activity of the 5-HT neurons, causing a dampening of the therapeutic effect. Studies suggest that after several weeks of SSRI administration, a desensitization of the 5-HT autoreceptors occurs allowing a full antidepressant effect in most patients, see Le Poul et al., *Arch. Pharmacol.*, 352:141 (1995). Hence, it is believed that overriding this negative feedback by using 5HT1A antagonists would increase and accelerate the clinical antidepressant response. Recent studies by Artigas et al., *Trends Neurosci.*, 19:378–383, (1996) suggest that a combination of 5-HT1A activity and inhibition of 5-HT uptake within a single molecular entity can achieve a more robust and fast-acting antidepressant effect.

The present invention relates to a new class of molecules which have the ability to act concomitantly at the 5-HT1A autoreceptors and with the 5-HT transporter. Such compounds are therefore potentially useful for the treatment of anxiety or depression, as well as other serotonin disorders.

U.S. Pat. No. 3,371,098 discloses sec. and tert. indolyl-ethylamines useful as sedatives, anticonvulsants and analegesics.

U.S. Pat. No. 5,436,264 discloses N-aryloxyalkyl-tryptamine-like compounds of the following formula as alpha-1-adrenergic receptor antagonists for the treatment of cardiovascular disorders.

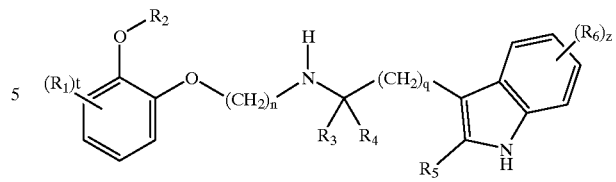

EP 0722 941 A2 discloses the preparation of a series of hetero-oxy alkanamines of the following formula for the treatment of depression and other disorders for which serotonin uptake inhibitors are normally used.

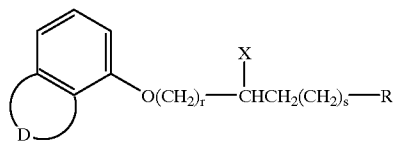

Japanese Patents 05255302 and 09040648 disclose the following compounds which are reported to be usefull for the treatment of central nervous system-related diseases, such as anxiety and depression.

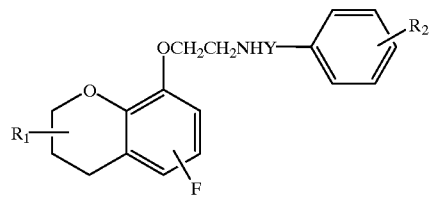

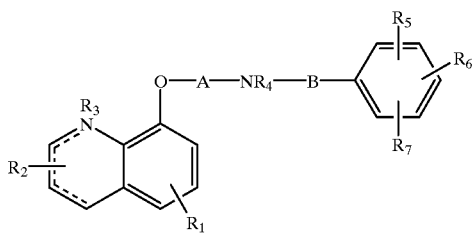

SUMMARY OF INVENTION

The compounds of the present invention invention are aminomethyl benzoxezine indoles represented by Formula I:

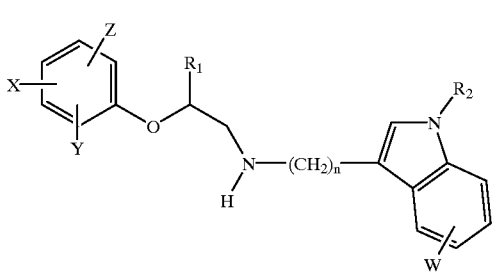

wherein:

$R_1$ is hydrogen, lower alkyl, or aryl;

$R_2$ is hydrogen, lower alkyl, phenyl, or substituted phenyl;

X and Y are each, independently, hydrogen, lower alky, lower alkoxy, or halogen, or together combine with the carbon atoms to which they are attached to complete a cyclopentyl, cyclohexyl, phenyl, pyrrolyl, pyranyl, pyridinyl, dihydrofuranyl, furanyl, dioxanyl, oxazolyl, or isoxazolyl group;

Z is hydrogen, halogen, or lower alkoxy; with the proviso that when X, Y or Z represent lower alkoxy, they are not present at the ortho position;

W is hydrogen, halogen, lower alkoxy, lower alkyl, cyano, or a trifluoromethyl group; and n is 2–5; or pharmaceutically acceptable salts thereof.

The present invention is further derived to pharmaceutical compounds containing such compounds, as well as methods for alleviating symptoms of depression comprising administering the present compounds to a patient in need thereof.

DETAILED DESCRIPTION OF THE INVENTION

Preferably, the compounds of the present invention are those represented by Formula I, wherein:

$R_1$ is hydrogen, methyl or aryl;

$R_2$ is hydrogen;

X and Y are each, independently, hydrogen, halogen or lower alkoxy, or together combine with the carbon atoms to which they are attached to complete a cyclopentyl, cyclohexyl, phenyl, pyridinyl, dioxanyl, oxazolyl, furanyl or dihydrofIranyl group;

Z is hydrogen, halogen or lower alkoxy; with the proviso that when X, Y or Z are lower alkoxy they are not present at the ortho position;

W is hydrogen or halogen; and n is 2–4; or pharmaceutically acceptable salts thereof Most preferably, the compounds of the present invention are selected from the following:

[3-(5-Fluoro-1H-indol-3-yl)-propyl]-[2-(1H-indol-4-yloxy)-ethyl]-amine;

[2-(1H-Indol-4-yloxy)ethyl]-[3-(1H-indol-3-yl)-propyl]-amine;

[3-(1H-Indol-3-yl)-butyl]-[2-(1H-indol-4-yloxy)-ethyl]-amine;

[2-(2,3-Dihydro-benzo[1,4]dioxin-5-yloxy)-ethyl]-[2-(1H-indol-3-yl)-ethyl]-amine;

[2-(2,3-Dihydro-benzo[1,4]dioxin-5-yloxy)-ethyl]-[3-(3-(5-fluoro-1-H-indol-3-yl)-propyl]-amine;

[2-(6-Fluorochroman-8-yloxy)-ethyl]-[2-(1H-indol-3-yl)-ethyl]-amine;

[2-(6-Fluorochroman-8-yloxy)-ethyl]-[3-(5-fluoro-1H-indol-3-yl)-propyl]-amine;

[2-(6-Fluorochroman-8-yloxy)-ethyl]-[2-(5-fluoro-1H-indol-3-yl)-ethyl]-amine;

[2-(2,3-Dihydro-benzofuran-7-yloxy)-ethyl]-3-(5-fluoro-1H-indol-3-yl)-propyl]-amine;

[2-(Benzofuran-7-yloxyethyl]-[3-(5-fluoro-1H-indol-3-yl)-propyl]-amine;

[2-(5-Fluoro-2,3-dihydro-7-yloxy-ethyl]-[2-(5-fluoro-1H-indol-3-yl)-ethyl]-amine;

[3-(5-Fluoro-1H-indol-3-yl)-propyl]-[2-(indan-4-yloxy)-ethyl]-amine;

[3-(5-Fluoro-1H-indol-3-yl)-propyl]-[2-(5,6,7,8-tetrahydro-naphthalen-1-yloxy)-ethyl]-amine;

[3-(1H-Indol-3-yl)-propyl]-[2-(naphthalen-1-yloxy)-ethyl] amine;

[3-(1H-Indol-3yl)-propyl]-(2-phenoxy-ethyl)-amine;

[3-(5-Fluoro-1H-indol-3yloxy)propyl]-[2-(indan-5yloxy)-ethyl]-amine;

[3-(1H-Indol-3-yl)-propyl]-[2-(quinolin-8-yloxy)-ethyl]-amine;

[3-(5-Fluoro-1H-indol-3-yl)-propyl]-[2-(2-methoxy-phenoxy)-2-phenyl-ethyl]-amine; and

[3-(5-Fluoro-1H-indol-3-yl)-propyl]-[2-(2-methoxy-phenoxy)-propyl]amine;

As used herein, the terms "lower alkyl" and "lower alkoxy" are meant to include both straight and branched carbon chains containing 1 to 6 carbon atoms. The term "halogen" is meant to include fluorine, chlorine, bromine, and iodine. The term "substituted phenyl" is meant to include a phenyl moiety substituted with an alkyl, halogen, or alkoxy group. The term "a;ryl" is meant to include aromatic radicals containing 6–12 carbon atoms.

The compounds of Formula I may advantageously be used in the form of the pharmaceutically acceptable acid addition salts thereof. Such salts, which may be prepared by methods well known to those skilled in the art, may be formed with both inorganic or organic acids, for example: fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnarnic, citraconic, aspartic, stearic, palmitic, itaconic, glycolic, p-minobenzoic, glutamic, benzene-sulfonic, hydrochloric hydrobrornic, sulfuric, cyclohexylsulfamic, phosphoric and nitric acids.

The compounds of the present invention may be prepared by any suitable method known to those skilled in the art. However, the present compounds may be advantageously prepared according to any one of Schemes 1 to 10 set forth below. In the Schemes, the intermediate compounds discussed hereinafter are identified in parenthesis. The compound produced in each of Schemes 1 to 10 is identified with reference to the appropriate, corresponding Example.

Scheme 1

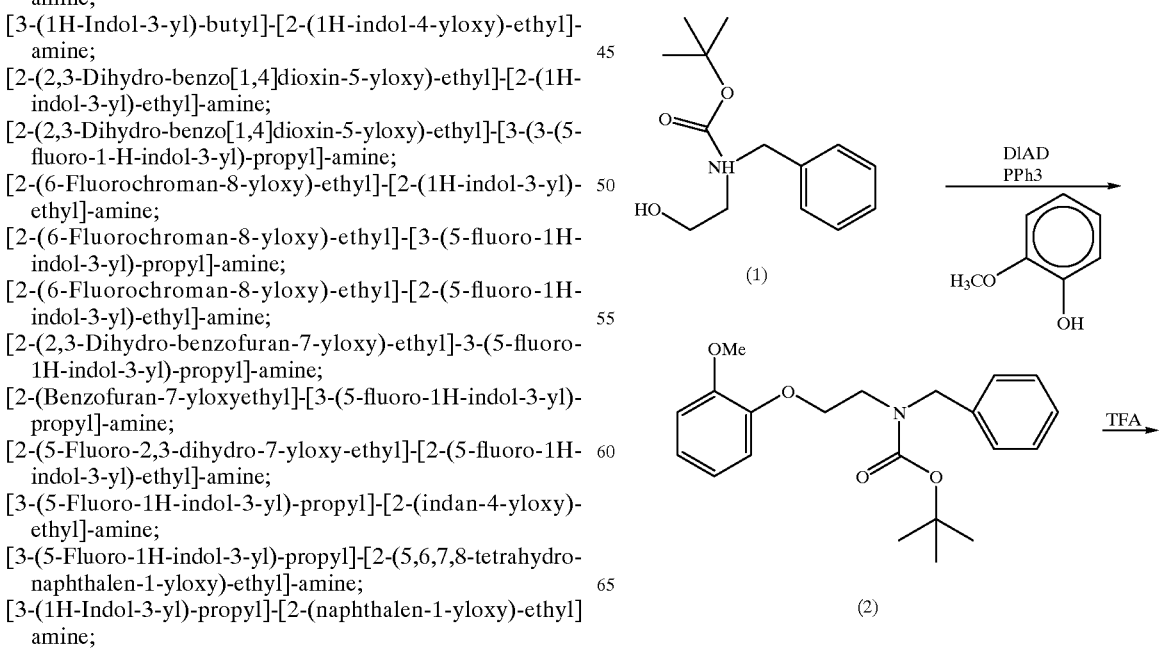

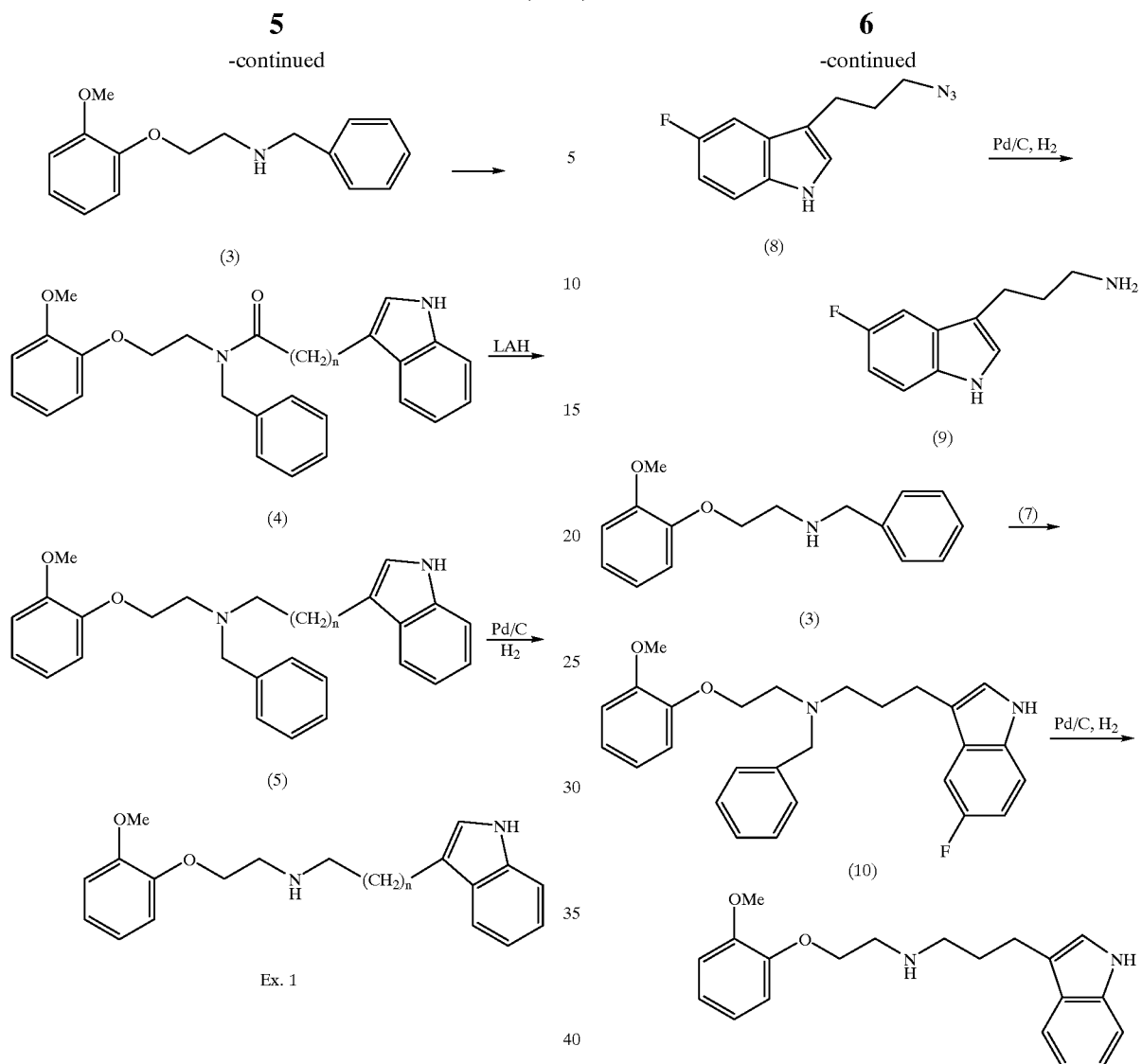
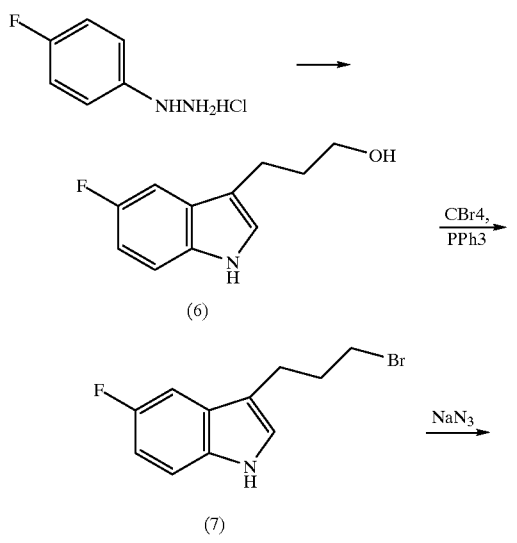
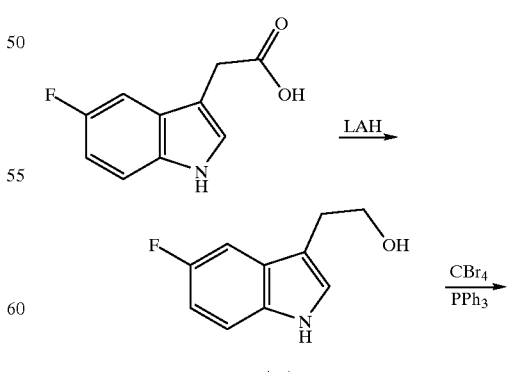

-continued
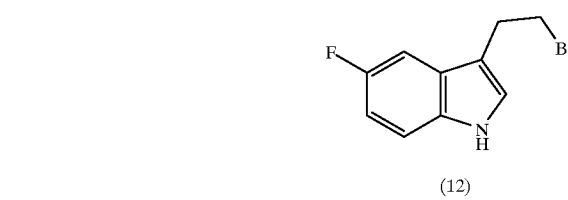
(12)
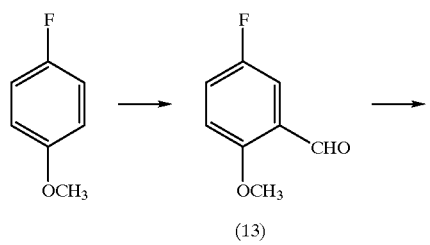
(13)
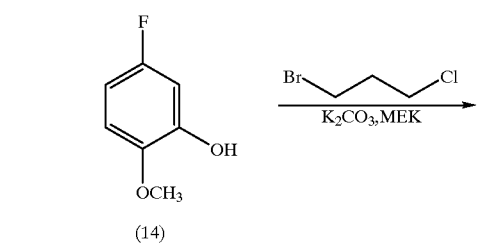
(14)
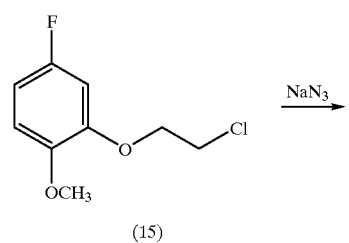
(15)
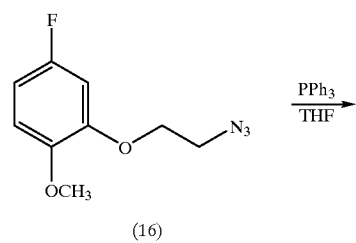
(16)
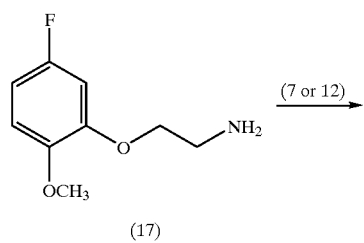
(17)
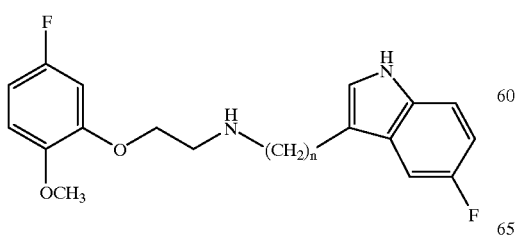
Ex. 3
-continued
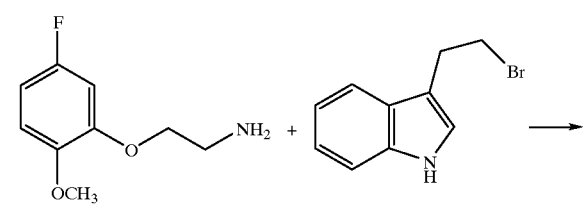
(17)     (12)
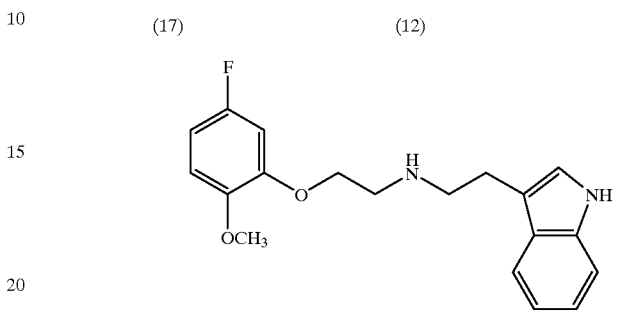
Ex. 4
Scheme 4
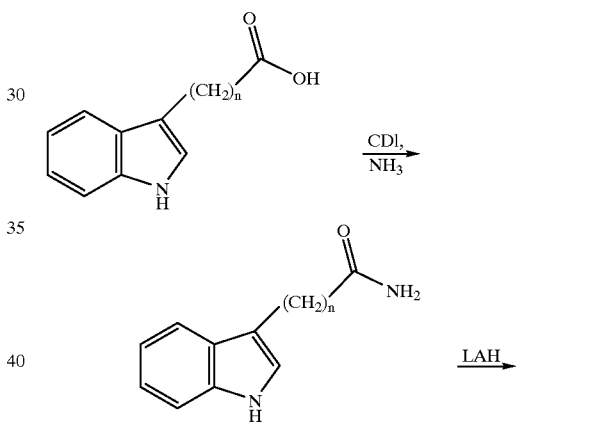
(18)
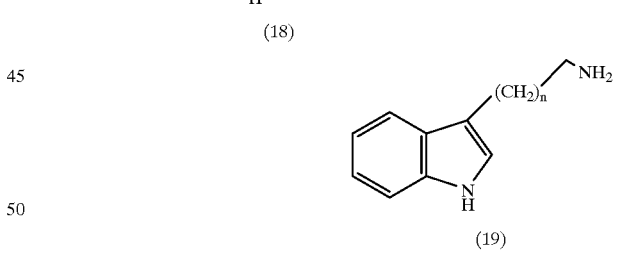
(19)
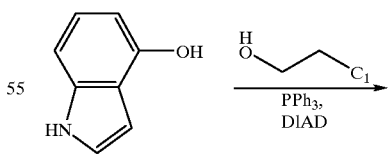
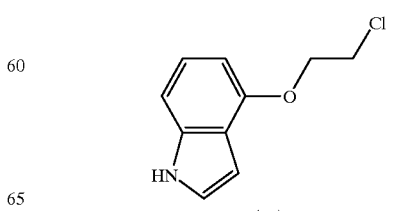
(20)

Scheme 5

(21) → (22) → (23) → (24) → Ex. 6

Scheme 6

(9) → Ex. 7

(25) → (26) → (27)

-continued
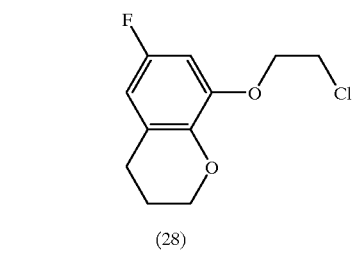
(28) → NaN₃ →
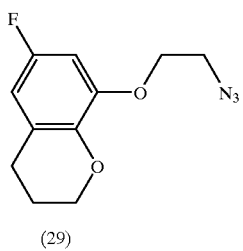
(29) → PPh₃ →
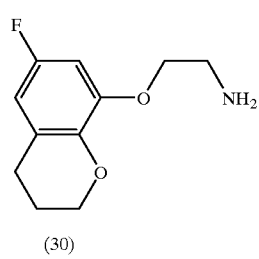
(30)
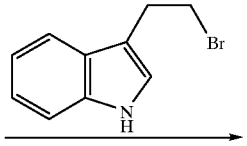
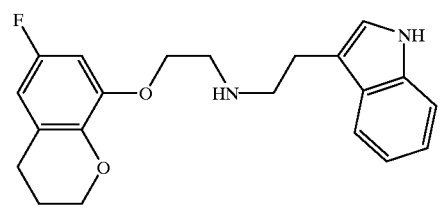
Ex. 8
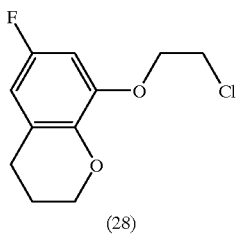
(28) → (7 or 12) →
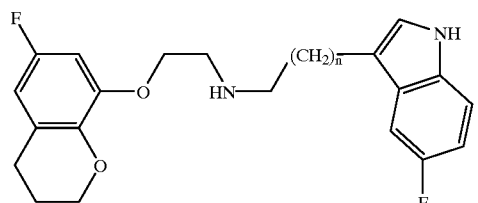
Ex. 9
Scheme 7
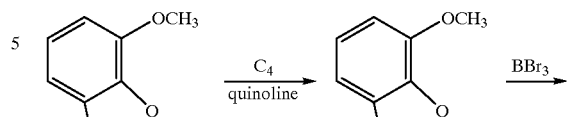 → C₄ / quinoline → 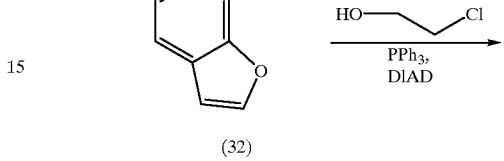 (31) → BBr₃ →
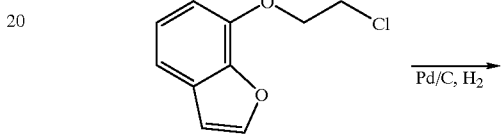 (32) → HOCH₂CH₂Cl / PPh₃, DIAD →
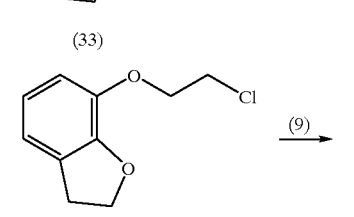 (33) → Pd/C, H₂ →
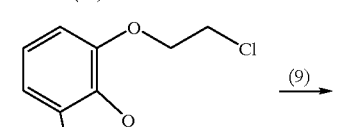 (34) → (9) →
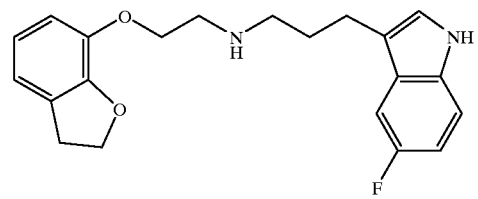
Ex. 10
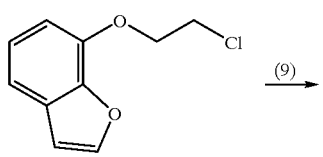 (34) → (9) →
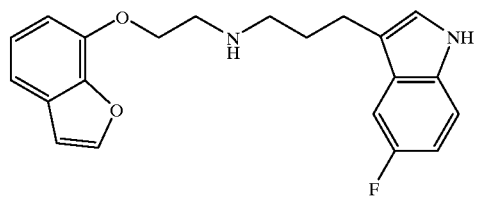
Ex. 11
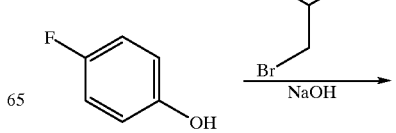 → EtO-CH(OEt)-CH₂Br / NaOH →

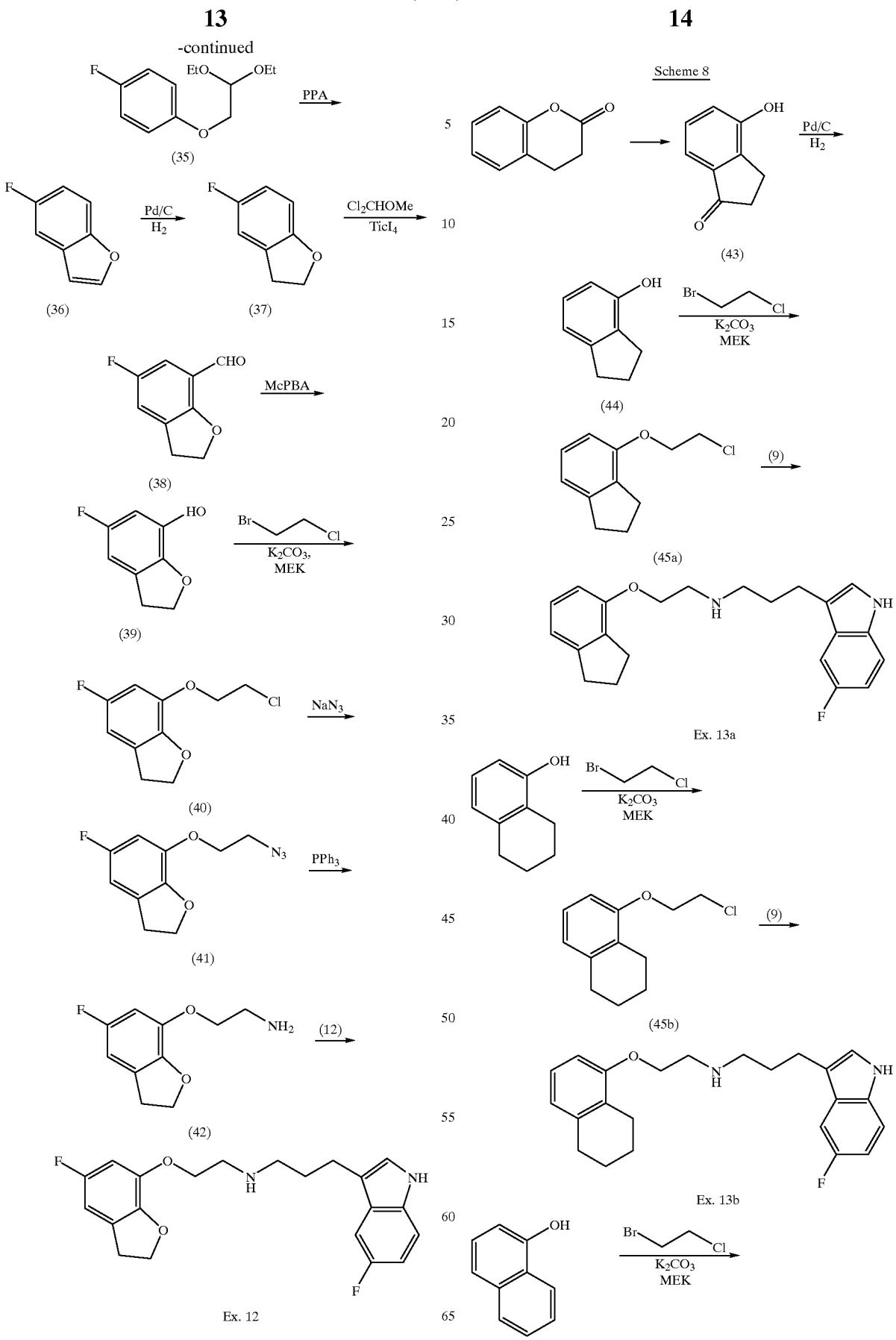

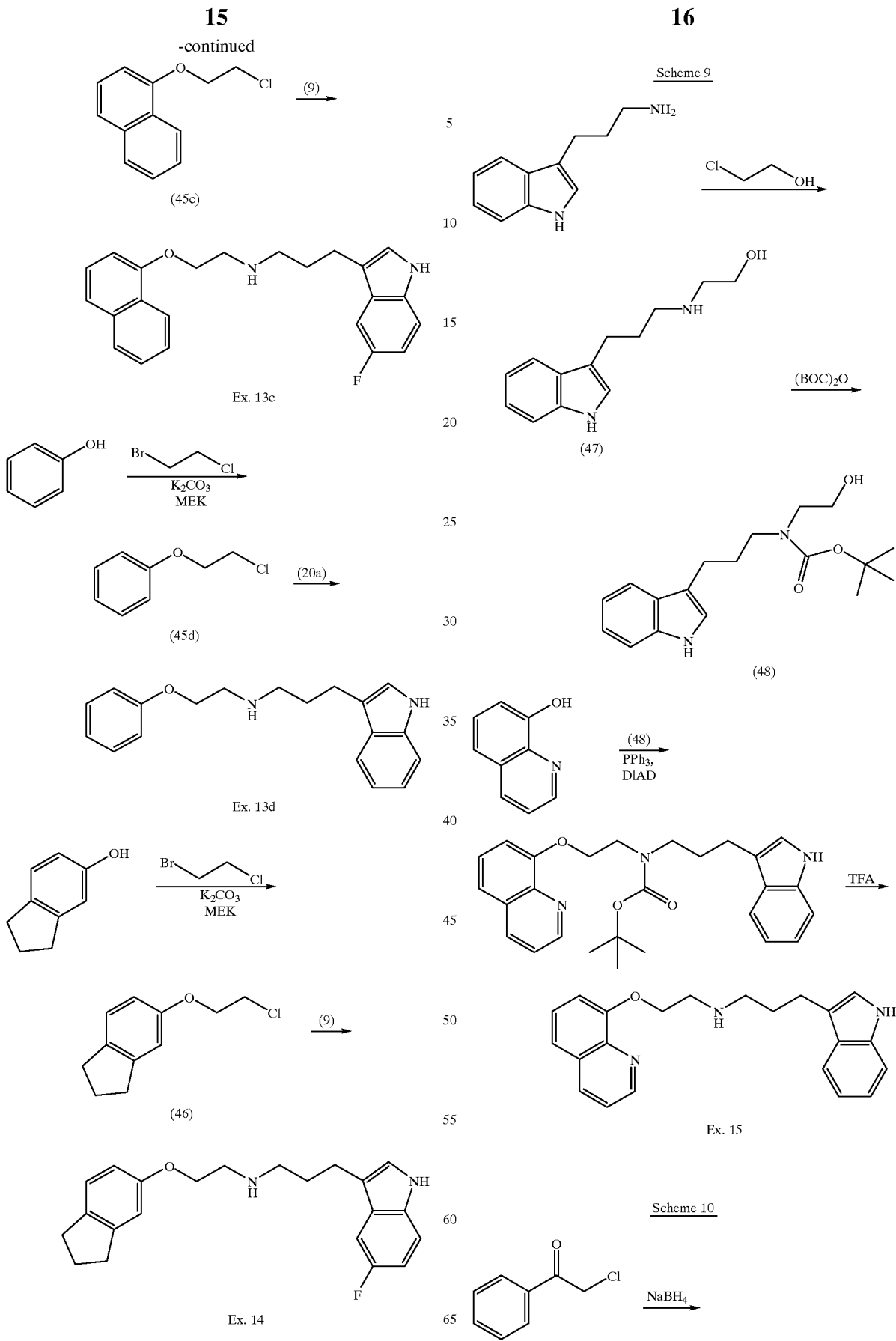

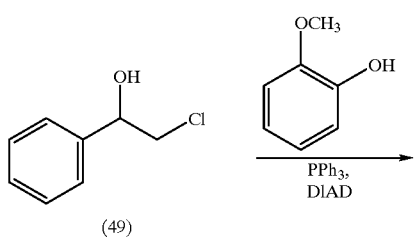

(49)

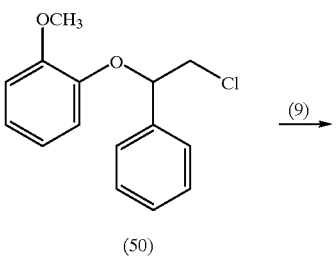

(50)

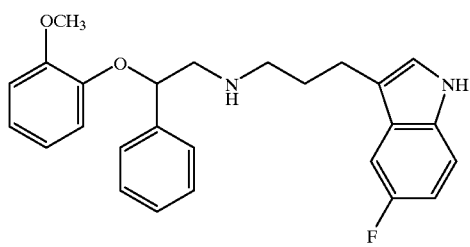

Ex. 16

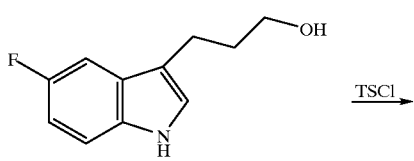

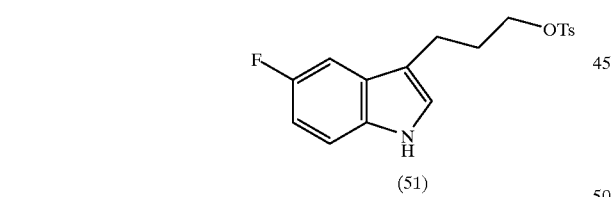

(51)

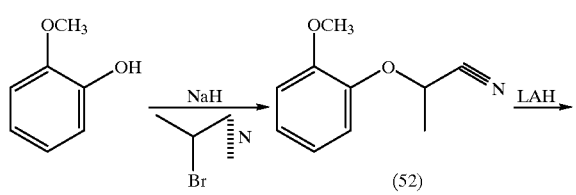

(52)

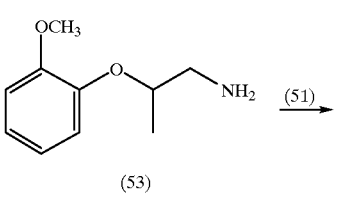

(53)

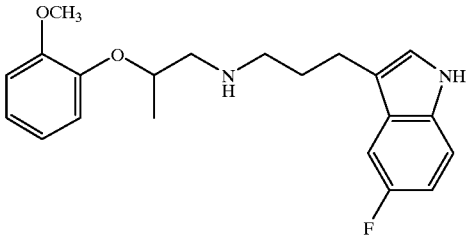

Ex. 17

The present invention will now be illustrated by reference to the following specific, non-limiting examples.

Intermediate 2

[2-(2-Methoxy-phenoxy-ethyl]-benzyl-carbamic acid tert-butyl ester

To a solution of (2-hydroxy-ethylfbenzyl-carbamic acid tert-butyl ester (3.2 g, 12.6 mmol) and 2-methoxy phenol (1.0 g, 8.4 mmol) containing triphenylphosphine (3.3 g, 12.6 mmol) in anhydrous tetrahydrofuran (40 ml) was slowly added diisopropyl azodicarboxylate (2.5 g, 12.6 mmol). The reaction was allowed to stir for 18 hours, then poured into methylene chloride (250 ml) and washed with 1N sodium hydroxide (3×80 ml), dried over anhydrous magnesium sulfate, filtered and concentrated to a clear oil. The oil was dissolved in ether (70 ml) and hexanes were slowly added until the triphenylphosphine oxide precipitated. The solid was filtered and the solvent removed. The thick oil was then purified by column chromatography (15% ethyl aceate-hexanes) to afford 2.57 g (57.0%) of a clear oil: MS (EI) 358 m/e (M+).

Elemental analysis for $C_{21}H_{27}NO_4$

Calc'd: C, 70.56; H, 7.61; N, 3.92

Found: C, 70.27; H, 7.58; N, 4.07

Intermediate 3

[2-(2-Methoxy-phenoxy)-ethyl]-benzyl-amine

To a solution of 2-(2-methoxy-phenoxy-ethyl]-benzyl-carbamic acid tert-butyl ester (18.0 g, 50.4 mmol) in methylene chloride (350 ml) was slowly added trifluoroacetic acid (60 ml). The reaction was stirred at room temperature for 12 hours, and then poured into 1N sodium hydroxide (200 ml) and extracted with methylene chloride (3×150 ml). The combined organic layers were washed with 1N sodium hydroxide (2×150 ml) followed by water (2×100 mL), then dried over anhydrous magnesium sulfate, filtered, and the solvent removed under vacuum. Chromatography (5% methanol-methylene choride) afforded 12.4 g (96%) of a clear oil.

Elemental analysis for $C_{16}H_{19}NO_2$

Calculated: C, 74.19; H, 7.24; N, 5.54

Found: C, 73.91; H, 7.28; N, 5.44

The fulmarate salt was prepared in ethanol: mp 121.5 –122° C.:

Elemental analysis for $C_{16}H_{19}NO_2 \cdot C_4H_4O_4$

Calc'd: C, 63.56; H, 6.27; N, 3.71

Found: C, 63.35; H, 6.16; N, 3.62

Intermediate 4

N-Benzyl-3-(1H-indol-3-yl)-N-[2-(2-methoxy-phenoxy)-ethyl]-propion-amide (4a)

To a solution of 3-indole propionic acid (4.1 g, 21.7 mmol) and 1-(3-dimethylamino-propyl)-3-ethylcarbodiimide hydrochloride (4.4 g, 23 mmol) in methylene chloride (80 ml) was added a solution of 2-(2-Methoxy-phenoxy)-ethyl-benzyl-aiine (3 g, 11.6 mmol) in methylene chloride (20 mnl) at 0° C. After 2 hours, the reaction mixture was poured into water (200 ml) and extracted with methylene chloride (2×50 ml). The combined organic layers were washed with 1N sodium hydroxide (50 ml), followed by water (2×50 ml). The organic layer was dried over anhydrous sodium sulfate, filtered, and the solvent removed under vacuum. Chromatography (5% methanol-methylene chloride) provided 3.3 g (66.0%) of product as a white solid: mp 46.5–47.5° C. MS EI m/e 428 (M$^+$)

N-Benzyl-3-(1H-indol-3-yl)-N-[2-(2-methoxy-phenoxy)-ethyl]-butyr-amide (4b)

Replacing 3-indole propionic acid with 3-indole butyric acid (1.8 g, 8.9 mmol) in (4a) above afforded N-benzyl-3-(1H-indol-3-yl)-N-[2-(2-methoxy-phenoxy)-ethyl]butyanide (1.3 g; 78%) as a white foam. MS FAB m/e 443 (M+H)$^+$ MS FAB m/e 465 (M+Na)$^+$

Inermediate 5

Benzyl-[3-(1H-indol-3-yl)-propyl]-[2-(2-methoxy-phenoxy)-ethyl]amine (5a)

To a solution of N-benzyl-3-(1H-indol-3-yl)-N-[2-(2-methoxy-phenoxy)-ethyl]-propion-amide in tetrahydrofuran (50 mL) at room temperature was added lithium aluminum hydride (1.8 g). The reaction was heated to reflux for 12 hours then allowed to cool to room temperature. The reaction was quenched with saturated ammonium chloride and the solid precipitates filtered through celite. The solvent was concentrated under vacuum and the product purified by chromatography (5% methanol-methylene chloride) to afford 2.0 g (86%) of product as a yellow oil. MS EI m/e 414 (M$^+$)

Elemental analysis for $C_{27}H_{30}N_2O$

Calc'd: C, 78.23; H, 7.30; N, 6.76

Found: C, 77.53; H, 6.95; N, 6.90

Benzyl-[4-(1H-indol-3-yl)-butyl]-[2-(2-methoxy-phenoxy)-ethyl]-amine (5b)

Replacing N-benzy-1-3-(1H-indol-3-yl)-N-[2-(2-methoxy-phenoxy)-ethyl]-propion-amide with N-benzyl-3-(1H-indol-3-yl)-N-[2-(2-methoxy-phenoxy)-ethyl]-butyl-amide (1.2 g, 2.7 mmol) in (5a) afforded N-benzyl-3-(1H-indol-3-yl)-N-[2-(2-methoxy-phenoxy)-ethyl]-butyl-amide (1.06 g, 91%) as a white oil. MS EI m/e 428 (M$^+$)

Intermediate 7

5-Fluoro-indolyl-3-propylbromide

A solution of 3-(5-fluoro-1H-indol-3-yl)-propan-1-ol (Intermediate 6) prepared in accordance with the procedures set forth in Demerson et al., *J. Med. Chem.*, 19:391–395 (1976). (25.4 g, 0.13 mol), carbon tetrabromide (65.5 g, 0.2 mol) and triphenylphosphine (52 g, 0.2 mol) in methylene chloride (156 ml) was allowed to stir for 2 hours. The solvent was evaporated and the product chromatographed (30% ethyl acetate-hexanes) to afford 33.5 g (99%) of product.

Intermediate 8

5-Fluoro-indolyl-3-propylazide

A solution of 5-fluoro-indolyl-3-propylbromide (10.67 g, 41 mmol) and sodium azide (3.9 g, 60 mmol) in anhydrous N,N-dimethylformamide (60 ml) was allowed to stir at 60° C. for 18 hours. The mixture was poured into water (150 ml), extracted with methylene chloride (3×150 ml), washed with water (3×100 ml). The organic layer was dried over sodium sulfate, filtered and the solvent was removed under vacuurml Chromatography (30% ethyl acetate-hexanes) afforded 8.10 g (89%) of product as a clear oil.

Elemental analysis for $C_{11}H_{11}FN_3$

Calc'd: C, 60.54; H, 5.08; N, 25.67

Found: C, 60.62; H, 5.08; N, 25.84

Intermediate 9

5-Fluoro-indolyl-3-propylamine

A solution of 5-fluoro-indolyl-3-propylazide (8 g, 0.037 mol) and 10% palladium on carbon in ethanol was hydrogenated at 50 psi for 16 hours. The catalyst was filtered and the solvent removed under vacuum. The celite was washed with methanol (300 ml) and the solvent was removed under vacuum. Chromatography (15% methanol-methylene chloride plus ammonium hydroxide) afforded 4.33 g (61%) of product as a yellow solid: mp 82–84.5° C.

Elemental analysis for $C_{11}H_{13}FN_2$

Calc'd: C, 68.73; H, 6.82; N, 14.57

Found: C, 68.82; H, 6.85; N, 14.49

Intermediate 10

[3-(5-Fluoro-1H-indol-3-yl)-propyl]-[2-(2-Methoxy-phenoxy) ethyl]-benzylamine

A solution of [2-(2-methoxy-phenoxy)ethyl]-benzyl-amine (1.0 g, 3.9 mol), 3-(5-fluoro-1H-indol-3-yl)-propylamine (1.4 g, 5.8 mmol) and triethylamine (0.79 g, 7.8 mmol) in dimethylsulfoxide (40 ml) was allowed to stir for 16 hours at 100° C. The reaction mixture was poured into water (100 ml) and extracted with methylene chloride (3×100 ml). The organic layer was washed with water (3–100 ml), dried over anhydrous sodium sulfate, filtered, and the solvent was removed under vacuum. Chromatography (30% ethyl acetate-hexanes) afforded 0.94 g (58%) of product as a yellow oil. MS EI m/e 432 (M$^+$)

Intermediate 11

2-(5-Fluoro-1H-indol-3-yl)ethanol

To a solution of 5-fluoro-indol-3-acetic acid (4.3 g, 0.022 mol) in anhydrous THF (35 ml) was added LiAlH$_4$(1.0M, 33 ml, 0.033 mol) at 0° C. The mixture was allowed to stir for 0.5 hours and, then quenched by saturated NH$_4$Cl solution. The mixture was then filtered through celite. The filtrate was washed with IN NaOH (3×100 ml) and extracted with ethyl acetate (3×100 ml). The organic layer was dried over anhydrous sodium sulfate, filtered, and the solvent was removed under vacuum. Chromatography (10% methanol-methylene chloride) afforded 4.04 g (100%) of product as an off-white solid: mp 59–61° C.

Elemental analysis for $C_{10}H_{10}FNO$
Calc'd: C, 67.03; H, 5.63; N, 7.82
Found: C, 66.71; H, 5.50; N, 7.74

Intermediate 12

3-(5-Fluoro-1H-indol-3-yl)-ethylbromide

To a solution of 2-(5-fluoro-1H-indol-3-yl)ethanol (4 g, 22.5 mmol) in methylene chloride (50 ml) was added carbon tetrabromide (11.2 g, 34 mmol), followed by triphenylphosphine (8.8 g, 33 mmol) at room temperature. The reaction mixture was allowed to stir at room temperature for 2.5 hours. The solvent was removed under vacuum. Chromatography (30% ethyl acetate-hexanes) afforded 5.91 g (98%) of product as an off-white solid: mp 58–59° C.

Elemental analysis for $C_{10}H_9FBrN$
Calc'd: C, 49.61; H, 3.75; N, 5.79
Found: C, 49.29; H, 3.73; N, 5.72

Intermediate 15

2-(5-Fluoro-2-methoxy-phenoxy)ethylchloride

A solution of 5-fluoro-2-methoxy-phenol (4.34 g, 31 nmol) prepared in accordance with the procedures set forth in Mancini et al., Synth. Comm., 19:2001–2005 (1989), 1-bromo-2-chloroethane (8.9 ml, 107 mmol) and potassium carbonate (14.8 g, 106 mmol) in 2-butanone (60 ml) was refluxed for 24 hours. The mixture was poured into water (150 ml), extracted with methylene chloride (3–150 ml) and washed with brine (3×100 ml). The organic layer was dried over sodium sulfate, filtered and the solvent was removed under vacuum. Chromatography (20% ethyl acetate-hexanes) afforded 4.77 g (76%) of product as a clear oil.

Elemental analysis for $C_9H_{10}FClO_2$
Calc'd: C, 52.83; H, 4.93
Found: C, 52.79; H, 4.75

Intermediate 16

2-(5-Fluoro-2-methoxy-phenoxy)ethylazide

A solution of 2-(5-fluoro-2-methoxy-phenoxy) ethylchloride (3.97 g, 19 mmol) and sodium azide (2.6 g, 39 mmol) in anhydrous N,N-dimethylformide (60 ml) was allowed to stir at 60° C. for 18 hours. The mixture was poured into water (150 ml), extracted with methylene chloride (3–150 ml), washed with water (3–100 ml). The organic layer was dried over sodium sulfate, filtered and the solvent was removed under vacuum. Chromatography (20% ethyl acetate-hexanes) afforded 3.75 g (92%) of product as a clear oil.

Elemental analysis for $C_9H_{10}FN_3O_2$
Calc'd: C, 51.18; H, 4.77; N, 19.90
Found: C, 51.35; H, 4.71; N, 20.06

Intermediate 17

2-(5-Fluoro-2-methoxy-phenoxy)ethylamine

A solution of 2-(5-fluoro-2-methoxy-phenoxy)ethylazide (3.97 g, 0.019 mol) and triphenylphosphine (5.95 g, 0.023 mol) in tetrahydrofuran (80 ml) and water (1.5 ml) was allowed to stir for 18 hours at room temperature. The solvent was removed under vacuum. Chromatography (ethyl acetate) removed triphenylphosphine and triphenylphosphine oxide and (25–50% methanol-ethyl acetate plus ammonium hydroxide) afforded 3.14 g (90%) of product as a clear oil. MS EI m/e 185 (M$^+$)

Intermediate 18

3-Indolyl-propionamide (18a)

A solution of 3-indolepropionic acid (15 g, 79 mmol), 1,1'-carbonyldimidazole (16.7 g, 100 mmol) in anhydrous tetrahydrofuran (150 ml) was allowed to stir for 1.5 hours at room temperature. Then NH$_3$ was bubbled through the solution for 2.5 hours at room temperature. The solvent was removed under vacuum, and the residue was dissolved in ethyl acetate (500 ml). The organic solution was washed with water (3×150 ml ), dried over anhydrous sodium sulfate, filtered, and the solvent was removed under vacuum. The white solid was collected and dried under vacuum 10.42 g (96%); mp 124–125° C. MS EI m/e 188 (M$^+$)

3-Indolyl-butyramide (18b)

This compound was prepared in the manner described above for (18a), using 3-indolebutyre acid and 1, 1'-carbonyldimidazole. A 96% yield was obtained as a off-white solid: mp 86–87° C.

Intermediate 19

3-Indolyl-propylamine (19a)

To a solution of 3-indolyl-propionamide (5 g, 24.7 mmol) in tetrahydrofuiran anhydrous (150 ml) was added lithium aluminum hydride (1.0M solution in tetrahydrofuran; 100 ml) slowly. The reaction mixture was refluxed for 3 hours, then was quenched by adding water (4 ml), 15% sodium hydroxide (4 ml) and water (12 ml) at 0° C. The mixture was filtered through celite and concentrated under vacuum. Chromatography (10% methanol-methylene chloride plus ammonium hydroxde) afforded 4.0 g (86%) of product as a white solid: mp 58–60.5° C. MS EI m/e 174 (M$^+$)

3-Indolyl-butylamine (19b)

This compound was prepared in in the manner described above for (19a) using 3-indolyl-butyramide and lithium aluminum hydride. A 75% yield was obtained as a yellow solid: mp 51–53° C.

Intermediate 20

2-(1H-Indol-4-yloxy)ethylchloride

To a solution of 4-hydroxyindole (4 g, 30 mmol), 2-chloroethanol (4.83 g, 60 mmol), triphenylphosphine (15.7 g, 60 mmol) in anhydrous tetrahydroufuran (40 ml) was slowly added diisopropyl azodicarboxylate (12.1 g, 60 mmol). The reaction was allowed to stir for 2.5 hours at room temperature, then poured into methylene chloride (250 ml), washed with water (3×100 ml) and dried over anhydrous sodium sulfate. This material was filtered and the solvent was removed under vacuum. Chromatography (20% hexanes-ethyl acetate) to remove triphenylphosphine, (20% methylene chloride-hexanes) afforded 2.94 g (50%) of product as a white solid: mp 69.5–72° C.

Intermediate 21

5-Hydroxy-(2,3)-dihydrobenzo[1,4]dioxine

Pyrogallol (5 g, 0.04 mol) was dissolved in 2-butanone (600 ml) to which potassium carbonate (1.82 g, 0.013 mol)

was added. The mixture was stirred at reflux while 1,2-dibromoethane (2.48 g, 1.14 ml, 0.013 mol) was slowly added dropwise. The reaction was allowed to stir overnight and then cooled to room temperature. The mixture was poured into water (100 ml) and extracted with methylene chloride (200 ml). The organic layer was dried over anhydrous sodium sulfate, filtered, and the solvent was removed under vacuum. Chromatography (5% methanol-methylene chloride) afforded 2.74 g (45%) of product as a clear oil. MS EI m/e 152 (M$^+$)

Intermediate 22

5-(2-Chloroethoxy)-(2,3)-dihydrobenzo[1,4]dioxane

To solution of 5-hydroxybenzodioxane (1.0 g, 6.5 mmol) and 2-chloroethanol (0.79 g, 9.9 mmol), triphenylphosphine (2.6 g, 9.9 mmol) in tetrahydrofliran (50 ml) was slowly added diisopropyl azidodicarbimide (DIAD) (2.0 g, 9.8 mmol). After 2 hours, another 1.5 eq of triphenylphosphine, DLAD, and 2chloroethanol was added thereto and the mixture stirred for another 2 hours. The reaction mixture was poured into water (100 ml), and extracted with methylene chloride (100 ml). The organic layer was separated and dried over anhydrous magnesium sulfate. This material was filtered, and the solvent removed under vacuum. Chromatography (20% ethyl acetate-hexanes) afforded 1.7 g (76%) of product as a white solid: mp 70.5–72.5° C.

Elemental analysis for $C_{10}H_{11}ClO_3$
Cal'd C, 55.96; H, 5.17
Found: C, 55.57; H, 5.20

Intermediate 23

2-(2,3-Dihydrobenzo[1,4]dioxin-5-yloxy)ethylazide

A solution of 5-(2-chloroethoxy)-(2,3)-dihydrobenzo[1,4]dioxane (4.6 g, 0.02 mol) and sodium azide (2.78 g, 0.043 mol) in anhydrous N,N-dimethyl-formamide (100 ml) was allowed to stir for 18 hours at 60° C. The mixture was poured into water (200 ml), extracted with methylene chloride (3×100 ml). The organic layer was washed with water (3×150 ml), dried over anhydrous sodium sulfate, filtered, and the solvent removed under vacuum. Chromatography (20% ethyl acetate-hexanes) afforded 3.43 g (72%) of product as a clear oil. MS FAB m/e 221 (M$^+$)

Intermediate 24

2-(2,3-Dihydrobenzo[1,4]dioxin-5-yloxy)ethylamine

A solution of 2-(2,3-dihydrobenzo[1,4]dioxin-5-yloxy) ethylazide (3.43 g, 0.016 mol) and triphenylphosphine (6.3 g, 0.023 mol) in tetrahydrofuran (50 ml) and water (2 ml) was allowed to stir for 18 hours at room temperature. The solvent was removed under vacuum. Chromatography (30% methanol-methylene chloride plus ammonium hydroxide) afford 1.93 g (62%) of product as a yellow oil. MS FAB m/e 196 (M+H)$^+$ Intermediate 25

6-Fluorochroman

A mixture of 6-fluoro-4chromanone (2 g, 12 mmol) and 10% palladium on carbon (1 g) in concentrated hydrochloric acid (20 ml) and ethanol (30 ml) was hydrogenated for 20 hours. The catalyst was filtered and the solvent removed under vacuum. The residue was dissolved in ethyl acetate (100 ml), washed with 1N NaOH (6×200 ml) and water (3×150 ml), dried over anhydrous sodium sulfate, filtered and the solvent was removed under vacuum. Chromatagraphy (20% ethyl acetate-hexanes) afforded 1.41 g (77%) of product as a clear oil. MS El m/e 152 (M$^+$)

Intermediate 26

6-Fluorochroman-8-carbaldehyde

To a solution of 6-fluorochroman (0.7 g, 4.6 mmol) in anhydrous methylene chloride (20 ml) was added $TiCl_4$ (1.57 g, 8.3 mmol) and α,α'-dichloromethyl methyl ether (0.53 g, 4.6 mmol) slowly at 0°C. The reaction was allowed to reach room temperature slowly and stirred for 16 hours. The reaction mixture was poured into ice-water, extracted with methylene chloride (3×100 ml), washed with saturated sodium carbonate (5×150 ml) and brine (3×100 ml). The organic layer was dried over anhydrous sodium sulfate, filtered, and the solvent was removed under vacuum. The crude solid was collected and dried under the vacuum to afford 0.75 g (90%) of product as a yellow solid: mp 55–57° C.

Elemental analysis for $C_{10}H_9FO_2$
Calc'd: C, 66.66; H, 5.04
Found: C, 66.64; H, 4.78

Intermediate 27

6-Fluoro-8-hydroxychroman

To a solution of 6-fluorochroman-8-carbaldehyde (8.6 g, 48 mmol), 3-t-butyl-4-hydroxy-5-methylphenyl sulfide (100 mg) in anhydrous methylene chloride (60 ml) at 0° C. was added 3-chloroperoxybenzoic acid (mCPBA) (12.4 g, 70 mmol) portionwise. The reaction mixture was allowed to reflux for 16 hours. The excess mCBPA was destroyed by adding 10% sodium sulfite. The benzoic acid was filtered and the filtrate was extracted with methylene chloride (3×150 ml) and washed with water (3×150 ml). The organic layer was dried over anhydrous sodium sulfate and filtered. The solvent was removed under vacuum and the crude product (10.2 g, 52 mmol) was dissolved in ethanol-water (200 ml, 1:1). To the above solution, sodium hydroxide (6.2 g, 160 mmol) was added at 0° C. After 30 minutes, the ice bath was removed, and the reaction mixture was allowed to stir for 3 hours at room temperature. Ethanol was then evaporated. The residue was neutralized with concentrated hydrochloric acid, extracted with methylene chloride (3×150 ml), washed with saturated sodium bicarbonate (2×100 ml) and brine (2×100 ml). The organic layer was dried over sodium sulfate, filtered and the solvent was removed under vacuum. Chromatography (25% ethyl acetate-hexanes) afforded 6.9 g (79%) of product as a white solid: mp 62–63° C.

Elemental analysis for $C_9H_9FO_2$
Calc'd. C, 64.28; H, 5.39
Found: C 641; H, 5.27

Intermediate 28

2-(6-Fluorochroman-8-yloxy)ethylchloride

A solution of 6-fluorochroman-8-carbaldehyde (5.5 g, 33 mmol), 1-bromo-2-chloroethane (16.4 g, 114 mmol) and $K_2CO_3$ (16 g, 114 mmol) in 2-butanone (60 ml) was refluxed for 24 hours. The mixture was poured into water (150 ml), extracted with methylene chloride (3×150 ml) and washed with brine (3×100 ml). The organic layer was dried over sodium sulfate, filtered and the solvent was removed under vacuum. Chromatography (20% ethyl acetate-hexanes) afforded 5.74 g of product as a white solid: mp 89–90° C.

Elemental analysis for $C_{11}H_{12}FO_2$
Calc'd: C, 57.28; H, 5.24
Found: C, 57.15; H, 5.69

Intermediate 29

2-(6-Fluorochroman-8-yloxy)ethylazide

A solution of 2-(6fluorochroman-8-yloxy)ethylchloride (4.13 g, 0.018 mol) and sodium azide (2.33 g, 0.036 mol) in anhydrous DMF (60 ml) was allowed to stir at 60° C. for 18 hours. The mixture was poured into water (150 ml), extracted with methylene chloride (3×150 ml) and washed with water (3×100 ml). The organic layer was dried over sodium sulfate, filtered and the solvent was removed under vacuum. Chromatography (20% ethyl acetate-hexanes) afforded 4.12 g (97%) of product as a clear oil.

Elemental analysis for $C_{11}H_{12}FN_3O_2$
Calc'd: C, 55.69; H, 5.10; N, 17.71
Found: C, 55.44; H, 4.97; N, 17.88

Intermediate 30

2-(6-Fluorochroman-8-yloxy)ethylamine

A solution of 2-(6-fluorochroman-8-yloxy)ethylazide (4.12 g, 0.017 mol) and triphenylphosphine (6.83 g, 0.026 mol) in tetrahydrofliran (80 ml) and water (1.5 ml) was allowed to stir for 18 hours at room temperature. The solvent was removed under vacuum. Chromatography (ethyl acetate) removed triphenylphosphine and triphenylphosphine oxide and (40% methanol-methylene chloride plus ammonium hydroxide) afforded 3.45 g (94%) of product as a white solid: mp 68–70° C.

Elemental analysis for $C_{11}H_{14}FNO_2$
Calc'd: C, 62.55; H,6.68; N, 6.63
Found: C,62.18; H, 6.54; N,6.63

Intermediate 31

7-Methoxybezofuran

A solution of 7-methoxy-2-benzofurancarboxylic acid (5 g, 0.026 mol), copper (0.2 g) in quinoline (30 ml) was heated under reflux for 2 hours. The mixture was filtrated through the celite. The celite was washed with ethyl acetate. The solvent was removed under vacuum. Chromatography (25% ethyl acetate-hexanes) afforded 2.45 g (64%) of product as a yellow oil. MS EI m/e 148 ($M^+$)

Intermediate 32

7-Hydroxybezofuran

7-Methoxybenzofliran (1 g, 6.7 mmol) was dissolved in anhydrous methylene chloride (25 ml) in a 100 ml round-bottom flask. The flask was placed in an acetone-ice bath at −78° C. The flask was fitted with a air-condenser. A solution of boron tribromide in methylene chloride (1 M, 10 ml) was added carefully to the stirred solution through the condenser. The reaction was kept at −78° C. for 6 hours and then was allowed to stir at room temperature overnight. The reaction was quenched by adding water (20 ml) and diluted with ethyl ether. The solvent was removed under vacuum. Chromatography (25% ethyl acetate-hexanes) afforded 0.47 g (52%) of product as a light-brown oil. MS EI m/e 134 ($M^+$)

Intermediate 33

2-(Benzofuran-7-yloxy)-ethylchloride

To a solution of 7-hydroxybenzofuran (0.47 g, 3.5 mmol), triphenyiphosphine (2.3 g, 8.7 mmol) and 2-chloroethanol (0.7 g, 8.7 mmol) in tetrahydrofuran ((50 ml) was slowly added dilsopropyl azodicarboxylate (1.8 g, 8.7 mmol). The reaction was stirred at room temperature for 3 hours. THF was removed under vacuum. Chromatography (25% ethyl acetate-hexanes) afforded 0.58 g, (84%) of product as a yellow oil. MS EI m/e 196 ($M^+$)

Intermediate 34

2-(2,3-Dihydrobenzofuran-7-yloxy)ethylchloride

A solution of 2-(enzoran-7-yloxy)-ethy(chloride (0.64 g) and 10% palladium on carbon in acetic acid (20 ml) was hydrogenated under 40 psi for 20 hours. The catalyst was filtered off and the solvent removed under vacuum. Chromatography (20% ethyl acetate-hexanes) afforded 0.39 g (60%) of product as a white solid: mp 49–52° C. MS EI m/e 198 ($M^+$)

Intermediate 35

2-(4-Fluorophenoxy)-acetaldehyde diethyl acetal

To a suspension of NaOH (5.4 g, 0.134 mol) in anhydrous DMF (100 ml) was added 4-fluorophenol (10 g, 0.089 mol) at 0° C. After $H_2$ evolution had ceased, bromo-acetaldehyde diethyl acetal (16 ml, 0.11 mol) was added. The reaction was heated at 160–170° C. for 18 hours. The mixture was poured into ice-water, extracted with ethyl acetate (3×150 ml), washed with 1N NaOH (3×100 ml) and brine (3×100 ml). The organic layer was dried over anhydrous sodium sulfate and filtered. The solvent was removed under vacuu. Chromatography (25% ethyl acetate-hexanes) afforded 16.36 g (80%) of product as a clear oil. MS EI m/e 228 ($M^+$)

Intermediate 36

5-Fluorobenzofuran

To a mixture of benzene (200 ml) containing polyphosphoric acid (7.9 g, 0.035 mol) was added 2-(4-fluorophenoxy)-acetaldehyde diethyl acetal (8 g, 0.035 mol). The mixture was stirred vigorously while being heated to reflux for 2.5 hours. The reaction mixture was cooled to room temperature and decanted from the polyphosphoric acid. The solvent was removed under vacuum. Chromatography (5% ethyl acetate-hexanes) afforded 3.4 g (45%) of product as a clear oil.

Intermediate 37

5-Fluoro-2,3-dihydrobenzofuran

A solution of 5-fluorobenzofuran and 10% palladium on carbon in acetic acid (25 ml) was hydrogenated under 50 psi for 12 hours. The catalyst was filtered through celite, and the celite was washed with methylene chloride (200 ml). The organic layer was washed with 1N NaOH (3×100 ml), brine (3×100 ml) and dried over anhydrous sodium sulfate. The solvent was removed under vacuum to afforded 2.59 g (85%) of product as a clear oil.

Intermediate 38

5-Fluoro-2,3-dihydrobenzofuran-7-carbaldehyde

To a solution of 5-fluoro-2,3-dihydrobenzofuran (7 g, 0.051 mol) in anhydrous methylene chloride (40 ml) was added $TiCl_4$ (9.5 ml, 0.087 mol), followed by α,α'-dichloromethyl methyl ether (4.6 ml, 0.051 mol) at 0° C. The reaction was allowed to reach room temperature slowly and stirred overnight. The reaction mixture was poured into ice-water slowly, extracted with methylene chloride (3×100 ml) and washed with saturated sodium carbonate (5×100 ml), and brine (3×100 ml). The organic layer was dried over anhydrous sodium sulfate and filtered. Chromatography (25% ethyl acetate-hexanes) afforded 3.29 g (39%) of product as a white solid: mp 103–104° C.

Elemental analysis for $C_9H_7FO_2$
Calc'd: C, 65.06; H, 4.75
Found: C, 65.01; H, 4.03

Intermediate 39

5-Fluoro-7-hydroxy-2,3-dihydro-benzofuran

To a solution of 5-fluoro-2,3-dihydrobenzofiran-7-carbaldehyde (3.29 g, 20 mmol), 3-t-buty-4-hydroxy-5-methylphenyl sulfide (100 mg) in anhydrous methylene chloride (40 ml) at 0° C. was added 3-chloroperoxybenzoic acid (mCPBA) (8.5 g, 30 mmol) portionwise. The reaction mixture was refluxed for 16 hours. The excess mCBPA was destroyed by adding 10% sodium sulfite. The benzoic acid was filtered off and the filtrate was extracted with methylene chloride (3×100 ml) and washed with water (3×100 ml). The organic layer was dried over anhydrous sodium sulfate and filtered. The solvent was removed under vacuum and crude product was dissolved in ethanol-water (100 ml, 1:1). To the above solution, sodium hydroxide (2.11 g, 53 nmuol) was added at 0° C. After 30 minutes, the ice bath was removed, and the reaction mixture was allowed to stir for 3 hours at room temperature. Ethanol was evaporated and the residue was neutralized with concentrated hydrochloric acid. This mixture was extracted with methylene chloride (3×100 ml) and washed with saturated sodium bicarbonate (2×100 ml) and brine (2×100 mml). The organic layer was dried over sodium sulfate, filtered and the solvent was removed under vacuum. Chromatography (30% ethyl acetate-hexanes) afforded 1.62 g (50%) of product as a white solid: mp 102.5–103.5° C.

Elemental analysis for $C_8H_7FO_2$
Calc'd: C, 62.34; H, 4.58
Found: C, 62.19; H, 4.59

Intermediate 40

2-(5-Fluoro-2,3-dihydro-benzofuran-7-yloxy) ethylchloride

A solution of 5-fluoro-7-hydroxy-2,3-dihydro-benzofuran (1.6 g, 10 mmol), 1-bromo-2-chloroethane (7.8 g, 55 mmol) and $K_2CO_3$ (2.2 g, 16 mmol) in 2-butanone (40 ml) was refluxed for 24 hours. The mixture was poured into water (150 ml), extracted with methylene chloride (3×150 ml) and washed with brine (3×100 ml). The organic layer was dried over anhydrous sodium sulfate, filtered and the solvent was removed under vacuum. Chromatography (25% ethyl acetate-hexanes) afforded 2.10 g of product as a white solid: mp 72.5–74.5° C.

Elemental analysis for $C_{10}H_{10}FClO_2$
Calc'd: C, 55.44; H, 4.65
Found: C, 55.37; H, 4.58

Intermediate 41

2-(5-Fluoro-2,3-dihydrobenzofuran-7-yloxy) ethylazide

A solution of 2-(5-fluoro-2,3-dihydrobenzofuran-7-yloxy)ethylchloride (2.05 g, 9.4 mmol) and sodium azide (1.23 g, 19 mol) in anhydrous DMF (30 ml) was allowed to stir at 60° C. for 24 hours. The mixture was poured into water (100 ml), extracted with methylene chloride (3×150 ml), washed with water (3×100 ml). The organic layer was dried over sodium sulfate, filtered and the solvent was removed under vacuum. Chromatography (20% ethyl acetate-hexanes) afforded 2.0 g (95%) of product as a clear oil. MS ESI m/e 241 [M+1]$^+$

Intermediate 42

2-(5-Fluoro-2,3-dihydrofuran-7-yloxy)ethylamine

A solution of 2-(5-fluoro-2,3-dihydrobenzofuran-7-yloxy)ethylazide (1.98 g, 89 mmol) and triphenylphosphine (2.8 g, 10.6 mmol) in tetrahydrofuran (50 ml) and water (1.5 ml) was allowed to stir for 18 hours at room temperature. The solvent was removed under vacuum. Chromatography (ethyl acetate) removed triphenylphosphine and triphenylphosphine oxide and (40% methanol-methylene chloride plus ammonium hydroxide) afforded 2.0 g (100%) of product as a clear oil. MS EI m/e 198 [M+1]$^+$

Intermediate 44

4-Indanol

A solution of 1 g of 2-(5-fluoro-2,3-dihydrofuran-7-yloxy)ethylamine (Intermediate 43) (Intermediate 44), prepared in the manner described by Ross et al., *J. Am. Chem. Soc.*, 110:6471–6480 (1988) and 10% palladium on carbon in acetic acid (50 ml), was hydrogenated for 36 hours. The catalyst was filtered off through celite. The celite was washed with methylene chloride. The organic layer was washed with saturated sodium carbonate (3×150 ml), brine (3×150 ml) and dried over sodium sulfate. The solvent was removed under vacuum. Chromatography (30% ethyl acetate-hexanes) afforded 0.78 g (86%) of product as a clear oil. MS EI m/e 134 (M$^+$)

Intermediate 45

2-(Indan-4-yloxy)-ethylchloride (45a)

To a solution of 4indanol (0.75 g, 5.6 mmol), triphenylphosphine (4.4 g, 16.8 mmol), 2-chloroethanol (0.7 g, 8.7 mmol) in tetrahydr6furan (50 ml) was slowly added diisopropyl azodicarboxylate (1.8 g, 8.7 mmol). The reaction was stirred at room temperature for 3 hours and the solvent was removed under vacuum. Chromatography (25% ethyl acetate-hexanes) afforded 0.58 g (84%) of product as a yellow oil. MS EI m/e 196 (M$^+$)

2-(5,6,7,8-Tetrahydronapthalen-1-yloxy)-ethylchloride (45b)

This compound was prepared in the manner described for 45(*a*) above by replacing 4-indanol with 5,6,7,8-tetrahydro-1-naphthol (4 g, 0.027 mol)) in 46% yield (2.57 g) as a clear oil.

Elemental analysis for $C_{12}H_{15}ClO$
Calc'd: C, 68.41; H, 7.17
Found: C, 68.37; H, 7.25

2-(Napthalen-1-yloxy)-ethylchloride (45c)

This compound was prepared in the manner described for 45(a) above by replacing 4-indanol with 1-naphthol (5 g, 0.035 mol)) in 82% yield (6.34 g) as a clear oil.

Elemental analysis for $C_{12}H_{11}ClO$
Calc'd: C, 69.74; H, 5.37
Found: C, 69.64; H, 5.30

2-Phenoxy-ethylchloride (45d)

This compound was prepared in the manner described above for 45(a) by replacing 4-indanol with phenol (5 g, 0.053 mol) in 12% yield (1.03 g) as a clear oil. MS EI m/e 156 ($M^+$)

Intermediate 46

2-(Indan-5-yloxy)-ethylchloride

A solution of 5-indanol (5 g, 0.037 mol), 1-bromo-2-chloroethanol (8.02 g, 0.056 mol) and potassium carbonate (7.7 g, 0.056 mol) in 2-butanone (40 ml) was refluxed for 18 hours. The mixture was poured into water (100 ml), extracted with methylene chloride (3×150 ml) and washed with water (3×100 ml). The organic layer was dried over anhydrous sodium sulfate, filtered and the solvent was removed under vacuum. Chromatography (20%o ethyl acetate-hexanes) afforded 3.2 g (43%) of product as a white solid: mp 45–46° C.

Elemental analysis for $C_{11}H_{13}ClO$
Calc'd: C, 67.18; H, 6.66
Found: C, 67.03; H, 6.57

Intermediate 47

[3-(1H-Indol-3-yl)-propyl]-(2-hydroxyethyl)amine

To a solution of 3-(1H-indol-3-yl)-propyl-amine (3.5 gV 18.6 mmol), 2-chloro-thanol (1 g, 12.4 mmol) in anhydrous dimethylsulfoxide (20 ml) was allowed to stir at 80° C. for 12 hours. The mixture was poured into water (100 ml), extracted with methylene chloride (3×150 ml) and washed with water (3×100 ml). The organic layer was dried over anhydrous sodium sulfate, filtered and the solvent was removed under vacuum. Chromatography (15% methanol-methylene chloride) afforded 1.04 g (38%) of product as a yellow oil. MS EI m/e 218 ($M^+$)

Intermediate 48

(2-Hydroxy-ethyl)-[3-(1H-indol-3-yI)-propyl]-carbamic acid-tert-butyl ester

A solution [3-(1H-indol-3-yl)-propyl]-(2-hydroxyethyl) amine (1.05 g, 4.5 mmol), di-tert-dicarbonate (5 g, 24 mmol) in anhydrous tetrahydrofliran (20 ml) was heated at 80° C. for 2 hours. The mixture was poured into water (100 ml), extracted with methylene chloride (3×150 ml) and washed with water (3×100 ml). The organic layer was dried over anhydrous sodium sulfate, filtered and the solvent was removed under vacuum. Chromatography (5% methanol-methylene chloride) afforded 0.86 g (56%) of product as a yellow oil. MS EI m/e 318 ($M^+$)

Intermediate 49

2-Chloro-1-phenylethanol

A solution of 2-chloroacetophenone (5 g, 0.032 mol), sodium borohydride (6.1 g, 0.16 mol) in tetrahydrofuran (30 ml) was allowed to stir at 60° C. for 18 hours. The reaction was quenched by water (200 ml) and stirred for another 2 hours. The mixture was extracted with methylene chloride (3×100 ml) and washed with water (3×150 ml). The organic layer was dried over sodium sulfate and filtered. The solvent was removed under vacuum and afforded 5.07 g(100%) of product as a clear oil. MS EI m/e 156 ($M^+$)

Intermediate 50

2-(2-Methoxy-phenoxy)-2-phenyl-ethylchloride

To a solution of guaiacol (2 g, 8.1 mmol), triphenylphosphine (6.4 g, 24 mmol), and 2chloro-1-phenylethanol (3.78 g, 24 mmol) in tetrahydrofuran (50 ml) was slowly added diisopropyl azodicarboxylate (4.8 g, 24 mmol). The reaction was stirred at room temperature for 2 hours. Tetrahydrofuran was removed under vacuum. Chromatography (20% ethyl acetate-hexanes) afforded 3.30 g (78%) of product as a clear oil. MS EI m/e 262 ($M^+$)

Intermediate 51

5-Fluoro-3-(3-p-toluenesulfonyloxypropyl)indole

To a stirred solution of 3-(5-fluoro-1H-indol-3-yl)-propan-l-ol (2.90 g, 15.0 mmol) in pyridine (15.0 mL) was added p-toluenesulfonyl chloride (7.1 g, 37.5 mmol) at room temperature. After stirring for 30 minutes at room temperature, the reaction mixture was poured to 200 nm of ice water. The aqueous was extracted with ethyl acetate and the combined organic extracts were washed with IN HCI and brine. The resulting material was dried over anhydrous sodium sulfate, filtered, and the solvent was concentrated under vacuum. The crude product was purified by silica gel column chromatography (ethyl acetatehexane, 3n) to give 4.1 g (79%) of the title compound as a solid: mp 74 CC (Lit. mp 99 ° C.; EP 464604 A2).

Intermediate 52

2-(2-Methoxy-phenoxy)propionitrile

To a solution of guaiacol (5 g, 0.04 mol) in anhydrous N,N-dimethylformide (20 ml) was added sodium hydride (1.16 g, 0.048 mol). The mixture was allowed to stir at room temperature for 0.5 hours, followed by the addition of 2-bromopropionitrile (8.09 g, 0.06 mol). The mixture was allowed to stir for 4 hours at room temperature and quenched with water (20 ml). The mixture was extracted with methylene chloride (3×100 ml), washed with water (3×100 ml) and the organic layer was dried over anhydrous sodium sulfate and filtered. The solvent was removed under vacuum. Chromatography (20% ethyl acetate-hexanes) afforded 3.91 g (55%) of product as a clear oil. MS EI m/e 177 $M^+$)

Intermediate 53

2-(2-Methoxy-phenoxy)propylamine

To a solution of 2-(2-methoxy-phenoxy)-propionitrile (3.91 g, 0.022 mol) in anhydrous ethyl ether (30 ml) was added lithium aluminum hydride (1.0 M, 44 ml, 0.044 mol). The mixture was heated at 65° C. for 18 hours and the reaction was quenched with water (3 ml), 15% NaOH (3 ml) and water (9 ml). The resulting material was filtered through celite. The celite was washed with methanol (200 ml), and the solvent was removed under vacuum. Chromatography (10% methanol-methylene chloride) afforded 0.26 g (7%) of product as yellow oil. MS EI m/e 181

EXAMPLE 1

[3-(1H-Indol-3-yl)-propyl]-[2-(2-methoxy-phenoxy)-ethyl]-amine

A mixture of benzyl-[3-(1H-indol-3-yl)-propyl]-[2-(2-methoxy-phenoxy)-ethyl]armine (2 g, 4.7 mmol) and 5% palladium on carbon in ethanol was hydrogenated for 20 hours. The catalyst was filtered off and the solvent removed under vacuum. Chromato-graphy (ethyl acetate-hexanes-methanol-ammonia hydroxide: 4/411/1) afforded 0.79 g (52%) of product as a white solid: mp 10I-102° C.

The fumurate salt was prepared in ethanol: mp 130–130.5° C.

Elemental analysis for $C_{20}H_{24}N_2O \cdot C_4H_4O_4$
Calc'd: C, 64.78; H, 6.46; N, 6.29
Found: C, 64.76; H, 6.23; N, 6.21

[4-(1H-Indol-3-yl)-butyl]-[2-(2-methoxy-phenoxy)-ethyl]-amine

Hydrogenation of benzyl-[4(1H-indol-3-yl)-butyl]-[2-(2-methoxy-phenoxy)-ethyl]-amine afforded 0.79 g (100%) of product as a clear oil. The oxalate salt was prepared from isopropanol: mp 167–168 ° C.

Elemental analysis for $C_{20}H_{24}N_2O_2 \cdot C_4H_4O_4$
Calc'd: C, 64.47; H, 6.59; N, 6.54
Found: C, 64.44; H, 6.52; N, 6.46

EXAMPLE 2

[3-(5-Fluoro-1H-indol-3-yl)-propyl]-[2-(2-Methoxy-phenoxy)ethyl]-amine

A mixture of [3-(5-fluoro1H-indol-3-yl)-propyl]-[2-(2-methoxy-phenoxy) ethyl]-benzylamine (0.94 g, 2.2 mol) and 10lo palladium on carbon (250 mg) in ethanol was hydrogenated for 20 hours. The catalyst was filtered off and the solvent was removed under vacuum. Chromatography (10% methanol-methylene chloride) afforded 0.63 g (85%) of product as an off-white solid: mp 125–126° C.

The oxalate salt was prepared in isopropanol: mp 146–149° C.

Elemental analysis for $C_{20}H_{23}FN_2O_2 \cdot C_2H_2O_4 \cdot 0.5H_2O$
Calc'd: C, 59.85; H, 5.94; N, 6.35
Found: C, 60.13; H, 5.67; N, 6.10

EXAMPLE 3

[3-(5-Fluoro-1H-indol-3-yl)propyl]-[2-(5-fluoro-2-methoxy-phenoxy)-ethyl]-amine A solution of 2-(5-fluoro-2-methoxy-phenoxy)ethylchloride (0.3 g, 1.5 mmol), 3-(5-fluoro-1H-indol-3-yl)propylamine (0.56 g, 2.9 mmol) in dimethylsulfoxide (20 ml) was allowed to stir for 12 h at 90° C. The reaction mixture was poured into water (100 ml) and extracted with methylene chloride (3×100 ml). The organic layer was washed with water (3×150 ml), dried over anhydrous sodium sulfate, filtered and the solvent was removed under vacuum. Chromatography (10% methanol-methylene chloride) afforded 0.39 g (77%) of product as a white solid: mp 119–122° C.

The oxalate salt was prepared in ethanol: mp 175–177° C.
Elemental analysis for $C_{20}H_{22}F_2N_2O_2 \cdot C_2H_2O_4$
Calc'd: C, 58.66; H, 5.57; N, 6.22
Found: C, 58.29; H, 5.25; N, 6.07

[2-(5-Fluoro-1l-indol-3-yl)ethyl]-[2-(5-fluoro-2-methoxy-phenoxy)-ethyl]-amine (3b)

A solution of 2-(5-fluoro-2-methoxy-phenoxy)ethylamine (0.51 g, 2.8 mmol), 2-(5-fluoro-1H-indol-3-yl)ethylchloride (0.44 g, 1.8 mmol) and thethylamine (0.29 g, 3 mmol) in dimethylsulfoxide (20 ml) was allowed to stir for 8 hours at 90° C. The reaction mixture was poured into water (100 ml) and extracted with methylene chloride (3×100 ml). The organic layer was washed with water (3×150 ml), dried over anhydrous sodium sulfate, filtered and the solvent was removed under vacuum. Chromatography (5% methanol-methylene chloride) afforded 0.27 g (43%) of product as a brown oil.

The oxalate salt was prepared in ethanol: mp 185–188° C.
Elemental analysis for $C_{19}H_{20}f_2N_2O_2 \cdot C_2H_2O_4$
Calc'd: C, 57.80; H, 5.08; N, 6.42
Found: C, 57.53; H, 4.95; N, 6.36

EXAMPLE 4

[2-(5-Fluoro-1H-indol-3-yl)ethyl]-[2-(5-fluoro-2-methoxy-phenoxy)-ethyl]-amine A solution of 2-(5-fluoro-2-methoxy-phenoxy)ethylamine (0.41 g, 2.2 mmol), 3-(2-bromoethyl)indole (0.25 g, 1.1 mmol) in dimethylsulfoxide (20 ml) was allowed to stir for 12 hours at 90° C. The reaction mixture was poured into water (100 ml) and extracted with methylene chloride (3×100 ml). The organic layer was washed with water (3×150 ml), dried over anhydrous sodium sulfate, filtered and the solvent was removed under vacuum. Chromatography (10% methanol-methylenc chloride) afforded 0.15 g (34%) of product as a brown oil.

The oxalate salt was prepared in ethanol: mp 188–189° C.
Elemental analysis for $C_{19}H_2 FN_2O_2 \cdot C_2H_2O_4 \cdot 0.25H_2O$
Calc'd C, 59.04; H, 5.63; N, 6.62
Found: C, 59.68; H, 5.49; N, 6.56

EXAMPLE 5

[3-(5-Fluoro-1H-indol-3-yl)propyl]-[2-(1 H-indol-4-yloxy)-ethyl]-amine

A solution of 2-(1H-indol4-yloxy)ethylchloride (0.7 g, 3.6 mmol), 5-fluoro-indolyl-3-propylamine (1.0 g, 5.4 mmol) in dimethylsulfoxide (20 ml) was allowed to stir for 12 hours at 90° C. The reaction mixture was poured into water (100 ml) and extracted with methylene chloride (3×100 ml). The organic layer was washed with water (3×150 ml), dried over anhydrous sodium sulfate, filtered and the solvent was removed under vacuum. Chromatography (5%–10% methanol-methylene chloride) afforded 0.54 g (43%) of product as a white solid: mp 70–73° C.

The oxalate salt was prepared in ethanol: mp 183.5–185° C.

Elemental analysis for $C_{21}H_{22}FN_3O \cdot C_2H_2O_4$
Calc'd C, 62.53; H, 5.48; N, 9.51
Found: C, 62.31; H, 5.38; N, 9.35

[2-(1H-Indol-4-yloxy)ethyl]-[3-(1H-indol-3-yl)-propyl]amine (5b)

This compound was prepared in the manner described above for Example 5 using 2-(1H-indolfyloxy)ethylchloride and 3-indolyl-propylamine in 65% yield as an off-white solid: mp 109–111° C. The oxalate salt was prepared in isopropanol: mp 200.5–202° C.

Elemental analysis for $C_{21}H_{23}N_3O \cdot C_2H_2O_4$
Calc'd: C, 65.19; H, 5.95; N, 9.92
Found: C, 64.89, H, 6.00; N, 9.81

[3-(1H-Indol-3-yl)butyl]-[2-(1H-indol-4-yloxy) ethyl]amine (5c)

This compound was prepared in the manner described above for Example 5 using 2-(1H-indol-4-yloxy) ethylchloride and 3-indolyl-butylamine in 43% yield as an off-white solid: mp 70–73° C.

The oxalate salt was prepared in ethanol: mp 183.5–185° C.

Elemental analysis for $C_{22}H_{25}N_3O \cdot C_2H_2O_4$
Calc'd: C, 62.58; H, 5.48; N, 9.52
Found: C, 62.31; H, 5.38; N, 9.35

EXAMPLE 6

[2-(2,3-Dihydrobenzo[1,4]dioxin-5-yloxy)-ethyl]-[2-(1H-indol-3-yl)-ethyl]-amine A solution of 2-(2,3-dihydrobenzo[1,4]dioxin-5-yloxy) ethylamine (0.38 g, 1.9 mmol), 3-(2-bromoethyl)-indole (0.24 g, 1.1 mmol) and triethylamine (0.22 g, 2.2 mmol) in anhydrous dimethylsulfoxide (20 ml) was allowed to stir for 14 hours at 90° C. The mixture was poured into water (100 ml) and extracted with methylene chloride (3×100 ml). The organic layer was washed with water (3×150 ml), dried over anhydrous sodium sulfate, filtered and the solvent was removed under vacuum. Chromatography (10% methanol-methylene choride plus ammonium hydroxide) afforded 0.19 g (52%) as a yellow oil.

The oxalate salt was prepared in ethanol: mp 197.5–198.5° C.

Elemental analysis for $C_{20}H_{22}N_2O_3 \cdot C_2H_2O_4$
Calc'd: C, 61.63; H, 5.64; N, 6.53
Found: C, 61.36; H, 5.46; N, 6.45s

EXAMPLE 7

[2-(2,3-Dihydro-benzo[1,4]dioxin-5-yloxy)-ethyl]-[3-(5-fluoro-1H-indol-3-yl)-propyl]-amine A solution of 5-(2-chloroethoxy)-(2,3)-dihydrobenzo [1,4]dioxane (0.75 g, 3.5 mmol), 3-(5-fluoro-1H-indol-3-yl)-propylanine (1.0 g, 5.2 mmol) and triethylarmine (0.35 g, 3.5 mmol) in anhydrous dimethylsulfoxide (20 ml) was allowed to stir for 14 hours at 100° C. The mixture was poured into water (100 ml) and extracted with methylene chloride (3×100 ml). The organic layer was washed with water (3×150 ml), dried over anhydrous sodium sulfate, filtered and the solvent was removed under vacuum. Chromatography (5%–10% methanol-methylene choride plus ammonium hydroxide) afforded 0.10 g (52%) of product as a yellow oil.

The fumurate salt was prepared in isopropanol: mp 189.5–190.5° C.

Elemental analysis for $C_{21}H_{23}FN_2O_3 \cdot 0.5C_4H_4O_4 \cdot 0.5H_2O$
Calc'd: C, 64.74; H, 5.88; N, 6.54
Found: C, 64.01; H, 5.95; N, 6.36

EXAMPLE 8

[2-(6-Fluorochroman-8-yloxy)ethyl]-[2-(1H-indol-3-yl)ethyl]-amine

A solution of 2-(6-fluorochroman-8-yloxy)ethylchloride (0.41 g, 2.2 mmol), 3-(2-bromoethyl)indole (0.25 g, 1.1 mmol) and triethylamine (0.23 g, 2.2 mmol) in anhydrous dimethylsulfoxide (20 ml) was allowed to stir for 12 hours at 90° C. The mixture was poured into water (100 ml) and extracted with methylene chloride (3×100 ml). The organic layer was washed with water (3×150 ml), dried over anhydrous sodium sulfate, filtered and the solvent was removed under vacuum. Chromatography (10% methanol-methylene choride plus ammonium hydroxide) afforded 0.15 g (34%) of product as a yellow oil.

The oxalate salt was prepared in ethanol: mp 213–214° C.

Elemental analysis for $C_{21}H_{23}FN_2O_2 \cdot C_2H_2O_4$
Calc'd: C, 62.11; H, 5.67; N, 6.30
Found: C, 62.26; H, 5.71; N, 6.19

EXAMPLE 9

[2-(6-Fluorochroman-8-yloxy)ethyl]-[3-(5-fluro-1H-indol-3-yl)propyl]-amine (9a)

A solution 2-(6-fluorochroman-8-yloxy)ethylchloride (0.25 g, 7.1 mmol), 3-(5-fluoro-1H-indol-3-yl)-propylamine (0.42 g, 2.2 mmol) and triethylamine (0.22 g, 2.2 mmol) in anhydrous dimethylsulfoxide (20 ml) was allowed to stir for 14 hours at 90° C. The mixture was poured into water (100 ml) and extracted with methylene chloride (3×100 ml). The organic layer was washed with water (3×150 ml), dried over anhydrous sodium sulfate, filtered and the solvent was removed under vacuum. Chromatography (10% methanol-methylene choride plus ammonium hydroxide) afforded 0.25 g (60%) as a white solid: mp 137–138.5° C.

The oxalate salt was prepared in isopropanol: mp 214–215° C.

Elemental analysis for $C_{22}H_{24}F_2N_2O_2 \cdot 1.5C_2H_2O_4$
Calc'd: C, 57.58; H, 5.22; N, 5.31
Found: C, 57.75; H, 5.07; N, 5.51

[2-(6-Fluorochroman-8-yloxy)ethyl]-[2-(5-fluro-1H-indol-3-yl)ethyl]-amine (9b)

A solution of 2-(6-fluorochroman-8-yloxy)ethylchloride (0.26 g, 1.1 mmol), 2-(5-fluoro-H-indol-3-yl)-ethylamine (0.45 g, 2.1 mmol) and triethylamine (0.30 ml, 2.1 mmol) in anhydrous dimethylsulfoxide (20 ml) was allowed to stir for 14 hours at 90° C. The mixture was poured into water (100 ml) and extracted with methylene chloride (3×100 ml). The organic layer was washed with water (3×150 ml), dried over anhydrous sodium sulfate, filtered and the solvent was removed under vacuum. Chromatography (10% methanol-methylene choride plus ammonium hydroxide) afforded 0.19 g (48%) of product as a yellow oil.

The oxalate salt was prepared in ethanol: mp 201–203° C.

Elemental analysis for $C_{21}H_{22}F_2N_2O_2 \cdot 1C_2H_2O_4$
Calc'd: C, 59.70; H, 5.23; N, 6.05
Found: C, 59.48; H, 5.08; N, 5.88

EXAMPLE 10

[2-(2,3-Dihydrobenzofuran-7-yloxy)ethyl]-[3-(5-fluoro-1-H-indol-3-yl)propyl]amine A solution of 2-(2,3-dihydrobenzofuran-7-yloxy) ethylchloride (0.38 g, 1.9 mmol), 3-(5-fluoro-1H-indol-3-yl)propylamine (0.93 g, 4.8 mmol), triethylamnine (0.48 g, 4.8 mmol) in anhydrous DMSO (20 ml) was allowed to stir at 90° C. for 12 hours. The mixture was poured into water (100 ml) and extracted with methylene chloride (3×100 ml). The organic layer was washed with water (3×150 ml), dried over anhydrous sodium sulfate, filtered and the solvent was removed under vacuum. Chromatography (10% methanol-methylene chloride plus ammonium hydroxide) afforded 0.52 g (77%) of product as a yellow oil.

The oxalate salt was prepared in ethanol: mp 158–160° C.
Elemental analysis for $C_{21}H_{23}FN_2O_2.C_2H_2O_4$
Calc'd: C, 63.82; H, 5.78; N, 5.95
Found: C, 63.45; H, 5.74; N,5.76

EXAMPLE 11

[2-(Benzofuran-7-yloxy)ethyl]-[3-(5-fluoro-1H-indol-3-yl)propyl]amine

A solution of 2-(benzofuran-7-yloxy)ethylchloride (0.58 g, 2.9 mmol), 3-(5-fluoro-1H-indol-3-yl)propylamine (1.4 g, 7.4 mmol) and triethylaniine (0.74 g, 7.4 mmol) in anhydrous DMSO (20 ml) was allowed to stir at 90° C. for 12 hours. The mixture was poured into water (100 ml) and extracted with methylene chloride (3×100 ml). The organic layer was washed with water (3×150 ml), dried over anhydrous sodium sulfate, filtered and the solvent was removed under vacuum. Chromatography (7% methanol-methylene chloride) afforded 0.31 g (30%) of product as a light-brown oil.

The oxalate salt was prepared in THF: mp 181–183° C.
Elemental analysis for $C_{21}H_{21}FN_2O_2.1C_2H_2O_4$
Calc'd: C, 62.39; H, 5.24; N, 6.33
Found: C, 62.07; H, 5.24; N, 6.45

EXAMPLE 12

[2-(5-Fluoro-2,3-dihydro-7-yloxy)-ethyl]-[2-(5-fluro-1H-indol-3-yl)-ethyl]-amine A solution of 2-(5-fluoro-2,3-dihydrofuran-7-yloxy) ethylamine (0.40 g, 2.1 mmol), 2-(5-fluoro-1H-indol-3-yl)-ethylamine (0.25 g, 1.0 mmol) and triethylamine (0.29 ml, 2.1 mmol) in anhydrous dimethylsulfoxide (20 ml) was allowed to stir for 14 hours at 90° C. The mixture was poured into water (100 ml) and extracted with methylene chloride (3×100 ml). The organic layer was washed with water (3×100 ml), dried over anhydrous sodium sulfate, filtered and the solvent was removed under vacuum. Chromatography (5% methanol-methylene choride plus ammonium hydroxide) afforded 0.2 g (54%) of product of product as a yellow oil.

The oxalate salt was prepared in ethanol: mp 209.5–210.5° C.
Elemental analysis for $C_{20}H_{20}F_2N_2O_2.1.5C_2H_2O_4$
Calc'd: C, 55.98; H, 4.70; N, 5.68
Found: C, 55.53; H, 4.44; N, 5.72

EXAMPLE 13

[3-(5-Fluoro-1H-indol-3-yl)-propyl]-[2-(indan-4-yloxy)-ethyl]-amine (13a)

A solution of 2-(indan4-yloxy)-ethylchloride (0.58 g, 2.9 mmol), 3-(5-fluoro-1H-indol-3-yl)-propylamine (1.4 g, 7.4 mmol) and triethylamine (1 ml, 7.4 mmol) in anhydrous dimethylsulfoxide (20 ml) was allowed to stir for 12 hours at 90° C. The mixture was poured into water (100 ml) and extracted with methylene chloride (3×100 ml). The organic layer was washed with water (3×100 ml), dried over anhydrous sodium sulfate, filtered and the solvent was removed under vacuum. Chromatography (7% methanol-methylene choride) afforded 0.31 g (30%) of product as a brown oil.

The oxalate salt was prepared in tetrahydrofuran: mp 220–222° C.
Elemental analysis for $C_{22}H_{25}FN_2O.C_2H_2O_4$
Calc'd: C, 65.10; H, 6.15; N, 6.33
Found: C, 64.74; H, 6.14; N, 6.11

[3-(5-Fluoro-1H-indol-3-yl)-propyl]-[2-(5,6,7,8-etrahydro-naphthalen-1-yloxy)-ethyl]-amine (13b)

This compound was prepared in the manner described above for Example 13 by replacing 2-(indan4-yloxy)-ethylchloride with 2-(5,6,7,8-tetrahydronapthalen-1-yloxy)-ethylchloride (0.6 g, 2.8 mmol) in 29% yield (0.3 g) as a yellow oil.

The fumurate salt was prepared in ethanol: mp 203–205° C.
Elemental analysis for $C_{23}H_{27}FN_2O.0.5C_4H_4O_4$
Calc'd: C, 70.73; H,6.89; N, 6.60
Found: C, 70.49; H, 6.87; N, 6.52

[3-(1H-indol-3-yl)-propyl]-[2-(naphthalen-1-yloxy)-ethyl]-amine (13c)

This compound was prepared in the manner described above for Example 13 by replacing 2-(indan-4-yloxy)-ethylchloride with 2-(napthalen-1 -yloxy)-ethylchloride (0.6 g, 2.8 mmol), and 3-(5-fluoro-1H-indol-3-yl)-propylamine with 3-(1H-indol-3-yl)-propylarmine (1.35 g, 7.2 mmol) in 85% yield (1.42 g) as a yellow solid: mp 119–120° C.

The fumurate salt was prepared in ethanol: mp 203–205° C.
Elemental analysis for $C_{23}H_{24}N_2O.0.5C_4H_4O_4.0.25H_2O$
Calc'd: C, 73.78; H,6.56; N, 6.88
Found: C, 73.74; H,6.47; N, 6.89

[3-(1H-indol-3-yl)-propyl]-[2-phenoxy-ethyl]-amine (13d)

This compound was prepared in the manner described above for Example 13 by replacing 2-(napthalen-1-yloxy)-ethylchloride with 2-phenoxy-ethylchloride (0.59 g, 3.8 mmol) in 100% yield (1.08 g) as a yellow oil.

The fumurate salt was prepared in ethanol: mp 203–205° C.
Elemental analysis for $C_{19}H_{22}N_2O.C_4H_4O_4$
Calc'd: C, 67.30; H, 6.38; N, 6.82
Found: C, 67.01; H, 6.30; N, 6.73

EXAMPLE 14

[3-(5-Fluoro-1H-indol-3-yloxy)-proyl]-[2-(indan-5-yloxy)-ethyl]-amine

A solution of 2(indan-5-yloxy)-ethylchloride (0.7 g, 3.5 mmol), 3-(5-fluoro-1H-indol-3-yl)-propylamine (1.01 g, 5.3 mmol) and triethylamine (0.53 g, 5 mmol) in anhydrous dimethylsulfoxide (20 ml) was allowed to stir for 12 hours at 90° C. The mixture was poured into water (100 ml) and extracted with methylene chloride (3×100 ml). The organic layer was washed with water (3×100 ml), dried over anhydrous sodium sulfate, filtered and the solvent was removed under vacuum. Chromatography (5–10% methanol-methylene choride) afforded 0.53 g (43%o) of product as a yellow oil.

The fumarate salt was prepared in ethanol: mp 179–180° C.

Elemental analysis for $C_{22}H_{25}FN_2O.0.5C_4H_4O_4$

Calc'd: C, 69.46; H, 6.68; N, 6.75

Found: C, 69.19; H. 6.67; N, 6.72

EXAMPLE 15

[3-(1H-Indol-3-yl)-propyl]-[2-(quinolin-8-yloxy) ethyl]-amine

To a solution of (2-hydroxy-ethyl)-[3-(1H-indol-3-yl)-propyl]-carbarnic acid-tert-butyl ester (0.86 g, 2.7 mmol), triphenylphosphine (0.71 g, 2.7 mmol) and 8-hydroxy-quinoline (0.26 g, 2.7 mmol) in tetrahydrofuran (50 ml) was slowly added diisopropyl azodicarboxylate (0.55 g, 2.7 mmol). The reaction was stirred at room temperature for 3 hours. Tetrahydrofuran was removed under vacuum. Chromatography (5% methanol-methylene chloride) afforded a yellow solid, which was dissolved in methylene chloride (30 ml). To this solution was added a trifluoroacetic acid solution (4 ml in 10 ml methylene chloride). The reaction rnixtrure was allowed to stir for 2 h at room temperature. The mixture was then quenched with saturated sodium carbonate and extracted with methylene chloride (3×100 ml). The organic layer was dried over anhydrous sodium sulfate and filtered. The solvent was removed under vacuum. Chromatography (10–15% methanol-methylene plus ammonium hydroxide) afforded 0.17 g (18%) of product as a light-yellow oil. The HCl salt was prepared in ethyl acetate: mp 83–86° C.

Elemental analysis for $CH_{22}H_{23}N_3O.HCl.1.25H_2O$

Calc'd: C, 65.34; H, 6.60; N, 10.39

Found: C, 65.24; H, 6.69; N, 10.47

EXAMPLE 16

[3-(5-Fluoro-1H-indol-3-yl)-propyl]-[2-(2-methoxy-phenoxy)-2-phenyl-ethyl]-amine A solution of 2-(2-methoxy-phenoxy)-2-phenyl-ethylchloride (0.71 g, 2.7 mmol), 2-(5-fluoro-1H-indol-3-yl)-ethylamine (1.04 g, 5.4 mmol) and triethylamine (0.75 ml, 5.4 mmol) in anhydrous dimethylsulfoxide (20 ml) was allowed to stir for 12 hours at 90° C. The mixture was poured into water (100 ml) and extracted with methylene chloride (3×100 ml). The organic layer was washed with water (3×100 ml), dried over anhydrous sodium sulfate, filtered, and the solvent was removed under vacuum. Chromatography (7% methanol-methylene choride plus ammonium hydroxide) afforded 0.15 g (13%)of product of product as a yellow oil. The citrate salt was prepared in ethyl ether: mp 64.5–67° C.

Elemental analysis for $C_{20}H_{20}F_2N_2O_2.C_6H_8O_7.1.5H_2O$

Calc'd: C, 60.27; H, 6.01; N, 4.39

Found: C, 59.96; H, 6.00; N, 4.39

EXAMPLE 17

[3-(5-Fluoro-1H-indol-3-yl)-propyl]-[2-(2-methoxy-phenoxy)propyl]amine

A solution of 2-(2-methoxy-phenoxy)propylamine (0.26 g, 1.2 mmol), 5-fluoro-3-(3-p-toluenesulfonyloxypropyl) indole (0.26 g, 0.81 mol) and triethylamine (0.13 g, 1.2 mmol) in anhydrous diethylsulfoxide (20 ml) was allowed to stir for 8 hours at 90° C. The mixture was poured into water (100 ml) and extracted with methylene chloride (3×100 ml). The organic layer was washed with water (3×100 ml), dried over anhydrous sodium sulfate, filtered and the solvent was removed under vacuum. Chromatography (10% methanol-methylene chloride plus ammonium hydroxide) afforded 0.1 g (36%) of product of product as a yellow oil.

The oxalate salt was prepared in 1-propanol: mp 143–146° C.

Elemental analysis for $C_{20}H_{20}F_2N_2O_2.C_2H_2O_4.1H_2O$

Calc'd: C, 59.47; H, 6.29; N, 6.03

Found: C, 59.34; H, 5.87; N, 5.96

The activity of the present compounds is demonstrated by the following standard pharmacological test procedures.

The PCR cloning of the human $5-HT_{1A}$ receptor subtype from a human genomic library has been described previously Chanda et al., *Mol. Pharmacol.,* 43:516 (1993). A stable Chinese hamster ovary cell line expressing the human $5-HT_{1A}$ receptor subtype ($5-HT_{1A}$.CHO cells) was employed throughout this study. Cells were maintained in DMEN supplemented with 10% fetal calf serum, non-essential amino acids and penicillin/ streptomycin.

Cells were grown to 95–100% confluency as a monolayer before membranes were harvested for binding studies. Cells were gently scraped from the culture plates, transferred to centrifuge tubes, and washed twice by centrifugation (2000 rpm for 10 min., 4° C.) in buffer (50 mM Tris; pH 7.5). The resulting pellets were aliquoted and placed at −80° C. On the day of assay, the cells were thawed on ice, and resuspended in buffer. Studies were conducted using [$^3$H]8-OH-DPAT as the radioligand. The binding assay was performed in 96 well microtiter plates in a final total volume of 250 $\mu$L of buffer. Competition experiments were performed by using 7 concentrations of unlabelled drug and a final ligand concentration of 1.5 nM. Non-specific binding was determined in the presence of 10 $\mu$M SHT. Saturation analysis was conducted by using [$^3$H]8-OH-DPAT at concentrations ranging from 0.3–30 nM. Following a 30 minute incubation at room temperature, the reaction was terminated by the addition of ice cold buffer and rapid filtration using a M-96 Brandel Cell Harvester (Gaithersburg, Md.) through a GF/B filter pre-soaked for 30 minutes in 0.5% polyethyleneimine.

A protocol similar to that used by Cheetham et al., *Neuropharmacol.* 32:737, (1993) was used to determine the affinity of compounds for the serotonin transporter. Briefly, frontal cortical membranes prepared from male Sprague-Dawley rats were incubated with $^3$H-paroxetine (0.1 nM) for 60 min at 25° C. All tubes also contained either vehicle, test compound (one to eight concentrations), or a saturating concentration of fluoxetine (10 $\mu$M) to define specific binding. All reactions are terminated by the addition of ice cold Tris buffer followed by rapid filtration using a Tom Tech filtration device to separate bound from free $^3$H-paroxetine. Bound radioactivity was quantitated using a Wallac 1205 Beta Plate® counter. Nonlinear regression analysis was used to determine $IC_{50}$ values which were converted to Ki values using the method disclosed in Cheng and Prusoff, *Biochem. Pharmacol.* 22:3099, (1973); Ki=IC50/((Radioligand conc.)/(1+KD)).

The [$^{35}$S]-GTPγS binding assay was similar to that disclosed by Lazareno and Birdsall, *Br. J. Pharmacol.,* 109:1120, (1993). Briefly, $5-HT_{1A}$ cloned receptor membrane fragments (as used for $5-HT_{1A}$ receptor binding assays) were stored at −70° C. until needed. When needed, membranes were rapidly thawed, centrifuged at 40,000 ×g for 10 minutes and resuspended at 4° C. for 10 minutes in assay buffer (25 mM HEPES, 3 mM $MgCl_2$, 100 mM NaCl, 1 mM EDTA, 10 $\mu$M GDP, 500 mM DTT, pH 8.0). These membranes were then incubated for 30 min at 30° C. with [$^{35}$S]GTPgS (1 nM) in the presence of vehicle, test compound (one to eight concentrations), or excess 8-OH-DPAT to define maximum agonist response. All reactions were terminated by the addition of ice cold Tris buffer followed by rapid filtration using a Tom Tech® filtration device to separate bound [$^{35}$S]GTPgS from free compound. Agonists produce an increase in the amount of bound [$^{35}$S]GTPgS whereas antagonists produce no increase in binding. Bound radioactivity was counted and analyzed as above.

The following assays were performed by incubating the cells with DMEM containing 25 mM HEPES, 5 mM theophylline and 10 $\mu$M pargyline for a period of 20 minutes at 37° C. Functional activity was assessed by treating the cells with forskolin (1 uM final concentration) followed immediately by test compound (6 concentrations) for an additional 10 min at 37° C. In separate experiments, 6 concentrations of antagonist were preincubated for 20 min prior to the addition of 10 nM 8-OH-DPAT and forskolin. The reaction was terminated by removal of the media and addition of 0.5 ml ice cold assay buffer. Plates were stored at −20 C. prior to assessment of cAMP formation by a cAMP SPA assay (Amersham).

The compounds tested correspond to those prepared in Examples 1 to 17 above. The results of the procedure are set forth in Table 1.

TABLE 1

| Example No. | 5-HT$_{1A}$ (Ki, nM) | ST(K$_i$, nM, or % Inhib. @ .1 $\mu$M) | GTP$\gamma$S ED$_{50}$ (EMax %) | cAMP ED$_{50}$ (EMax %) |
|---|---|---|---|---|
| 1a | 1.97 | 22 | 13.0 (80%) | 1.32 (94%) |
| 1b | 7.72 | 25 | 44.0 (60%) | — |
| 2 | 1.34 | 0.48 | 41.6 (77%) | 4.28 (97%) |
| 3a | 35.0 | 0.97 | — | 4.71 (99%) |
| 3b | 47.9 | 49% | (100)% | — |
| 4 | 91.4 | 28.0 | — | — |
| 5a | 1.50 | 0.57 | 2.0 (90%) | — |
| 5b | 2.47 | 14 | 4.0 (66%) | — |
| 5c | 4.22 | 18 | 25.8 (59%) | — |
| 6 | 5.80 | 12.0 | (100%) | — |
| 7 | 0.68 | 0.08 | 15.7 (75%) | 1.11 (90%) |
| 8 | 8.53 | 4.5 | 36 (49%) | — |
| 9a | 26.6 | 0.84 | 121 (0%) | 49 (0%) |
| 9b | 29.2 | 4.5 | — | 234 (0%) |
| 10 | 1.63 | 0.74 | 4.72 (80%) | — |
| 11 | 1.55 | 3.03 | 2.93 (99.9%) | — |
| 12 | 35.1 | 12.0 | — | — |
| 13a | 76.9 | 71% | — | — |
| 13b | 170.3 | 40 | — | — |
| 13c | 16.8 | 34% | — | — |
| 13d | 9.20 | 26% | — | — |
| 14 | 158.4 | 56 | — | — |
| 15 | 0.54 | 24 | 3.0 (76%) | — |
| 16 | 43.9 | 21.0 | — | — |
| 17 | 14.50 | 16.0 | 236 (97.5%) | — |

As demonstrated by the results set forth above, the compounds of the present ion are active towards 5HT1A receptors and generally elevate serotonin levels by inhibiting 5-HT transport. Accordingly, the present compounds should be useful in treating disorders related to defects in serotonin concentration.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the fmely divided active ingredient. In tablets, the active ingredient is mixed with a carrier having the necessary compression properties in suitable proportions and compacted in the shape and size desired. The powders and tablets preferably contain up to 99% of the active ingredient. Any of the solid carriers known to those skilled in the art may be used with the compounds of this invention. Particularly suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidone, low melting waxes and ion exchange resins.

Liquid carriers may be used in preparing solutions, suspensions, emulsions, syrups and elixirs of the compounds of this invention. The compounds of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) and their derivatives and oils (e.g., fractionated coconut oil and arachis oil). For parenteral administration, the carrier can also be an oily ester such as ethyl oleate and isopropyl myristate. Sterile liquid carriers are used to prepare compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Compositions for oral administration may be either in liquid or solid composition form.

Preferably, the pharmaceutical compositions containing the compounds of this invention are in unit dosage form, e.g., tablets or capsules. In such form, the compositions may be subdivided in unit doses containing appropriate quantities of the present compounds. The unit dosage forms can be packaged compositions, for example, packeted powders, vials, ampoules, prefilled syringes or sachets containing liquids. Alternatively, the unit dosage form can be, for example, a capsule or tablet itself, or it can be the appropriate number of any such compositions in package form.

The therapeutically effective amount of the compounds of this invention that is administered and the dosage regimen depends on a variety of factors, including the weight, age, sex, and medical condition of the subject, the severity of the disease, the route and frequency of administration, and the specific compound employed, and thus may vary widely. However, it is believed that the pharmaceutical compositions may contain the compounds of this invention in the range of about 0.1 to about 2000 mg, preferably in the range of about 0.5 to about 500 mg and more preferably between about 1 and about 100 mg. Projected daily dosages of active compound are about 0.01 to about 100 mg/kg body weight. The daily dose can be conveniently administered two to four times per day.

The present invention may be embodied in other specific forms without departing from the spirit and essential attributes thereof and accordingly, reference should be made to the appended claims, rather than to the foregoing specification, as indicating the scope of the invention.

What is claimed is:

1. A compound formula:

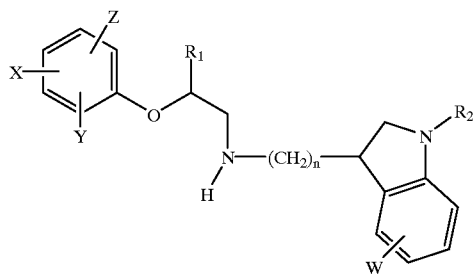

wherein:

$R_1$ is hydrogen, lower alkyl or aryl;

$R_2$ is hydrogen, lower alkyl, phenyl or substituted phenyl;

X and Y are each, independently, hydrogen, lower alkyl, or halogen, or together combine with the carbon atoms to which they are attached to complete a cyclopentyl, cyclohexyl, or phenyl group;

Z is hydrogen or halogen;

W is hydrogen, halogen, lower alkyl, cyano or a trifluoromethyl group; and n is 2–5; or pharmaceutically acceptable salts thereof.

2. A compound as in claim 1, wherein:

$R_1$ is hydrogen, methyl or aryl;

$R_2$ is hydrogen;

X and Y are each, independently, hydrogen or halogen, or together combine with the carbon atoms to which they are attached to complete a cyclopentyl, cyclohexyl, or phenyl group;

Z is hydrogen or halogen;

W is hydrogen or halogen; and n is 2–4; or pharmaceutically acceptable salts thereof.

3. The compound of claim 1, which is [3-(5-Fluoro-1H-indol-3-yl)-propyl]-[2-(indan-4-yloxy)-ethyl]-amine.

4. The compound of claim 1, which is [3-(5-Fluoro-1H-indol-3-yl)-propyl]-[2-(5,6,7,8-tetrahydro-naphthalen-1-yloxy)-ethyl]-amine.

5. The compound of claim 1, which is [3-(1H-Indol-3-yl)-propyl]-[2-(naphthalen-1-yloxy)-ethyl]amine.

6. The compound of claim 1, which is [3-(1H-Indol-3yl)-propyl]-(2-phenoxy-ethyl)-amine.

7. The compound of claim 1, which is [3-(5-Fluoro-1H-indol-3-yl)-propyl]-[2-(2-methoxy-phenoxy)-2-phenyl-ethyl]-amine.

8. The compound of claim 1, which is [3-(5-Fluoro-1H-indol-3-yl)-propyl]-[2-(2-methoxy-phenoxy)-propyl]amine.

9. A pharmaceutical composition comprising a compound of the formula:

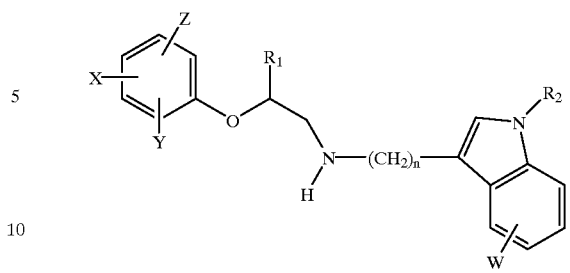

wherein:

$R_1$ is hydrogen, lower alkyl or aryl;

$R_2$ is hydrogen, lower alkyl, phenyl or substituted phenyl;

X and Y are each, independently, hydrogen, lower alkyl, or halogen, or together combine with the carbon atoms to which they are attached to complete a cyclopentyl, cyclohexyl, phenyl, group;

Z is hydrogen or halogen

W is hydrogen, halogen, lower alkyl, cyano or a trifluoromethyl group; and n is 2–5; or pharmaceutically acceptable salts thereof.

10. A method for alleviating the symptoms of depression in a patient in need thereof comprising administering to said patient an antidepressant effective amount of a compound of the formula:

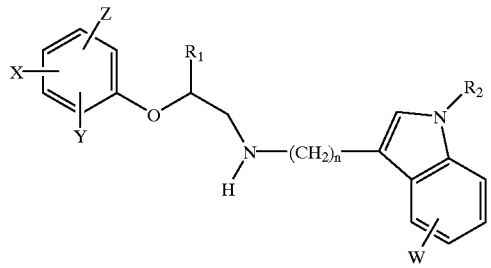

wherein:

$R_1$ is hydrogen, lower alkyl or aryl;

$R_2$ is hydrogen, lower alkyl, phenyl or substituted phenyl;

X and Y are each, independently, hydrogen, lower alkyl, or halogen, or together combine with the carbon atoms to which they are attached to complete a cyclopentyl, cyclohexyl, phenyl, group;

Z is hydrogen or halogen

W is hydrogen, halogen, lower alkyl, cyano or a trifluoromethyl group; and n is 2–5;or pharmaceutically acceptable salts thereof.

* * * * *